(12) United States Patent
Flanner et al.

(10) Patent No.: US 8,778,924 B2
(45) Date of Patent: *Jul. 15, 2014

(54) MODIFIED RELEASE AMOXICILLIN PRODUCTS

(75) Inventors: Henry H. Flanner, Montgomery Village, MD (US); Sanna Tolle-Sander, North Potomac, MD (US); Donald Treacy, Woodbine, MD (US); Beth A. Burnside, Bethesda, MD (US); Susan P. Clausen, Ijamsville, MD (US)

(73) Assignee: Shionogi Inc., Florham Park, NJ (US)

( * ) Notice: Subject to any disclaimer, the term of this patent is extended or adjusted under 35 U.S.C. 154(b) by 1239 days.

This patent is subject to a terminal disclaimer.

(21) Appl. No.: 11/633,315

(22) Filed: Dec. 4, 2006

(65) Prior Publication Data

US 2008/0132478 A1 Jun. 5, 2008

(51) Int. Cl.
*A61K 31/43* (2006.01)

(52) U.S. Cl.
USPC ........................................................ 514/197

(58) Field of Classification Search
None
See application file for complete search history.

(56) References Cited

U.S. PATENT DOCUMENTS

| | | | |
|---|---|---|---|
| 3,108,046 A | 10/1963 | Harbit | |
| 1,330,829 A | 5/1972 | Wilson | |
| 3,870,790 A | 3/1975 | Lowey et al. | |
| 4,007,174 A | 2/1977 | Laundon | |
| 4,008,246 A | 2/1977 | Ochiai et al. | |
| 4,018,918 A | 4/1977 | Ayer et al. | |
| 4,048,306 A | 9/1977 | Maier et al. | |
| 4,131,672 A | 12/1978 | Huffman | |
| 4,175,125 A | 11/1979 | Huffman | |
| 4,226,849 A | 10/1980 | Schor | |
| 4,236,211 A | 11/1980 | Arvesen | |
| 4,250,166 A | 2/1981 | Maekawa et al. | |
| 4,331,803 A | 5/1982 | Watanabe et al. | |
| 4,362,731 A | 12/1982 | Hill | |
| 4,369,172 A | 1/1983 | Schor et al. | |
| 4,399,151 A | 8/1983 | Sjoerdsma et al. | |
| 4,430,495 A | 2/1984 | Patt et al. | |
| 4,435,173 A | 3/1984 | Siposs et al. | |
| 4,474,768 A | 10/1984 | Bright | |
| 4,517,359 A | 5/1985 | Kobrehel et al. | |
| 4,525,352 A | 6/1985 | Cole et al. | |
| 4,529,720 A | 7/1985 | Cole et al. | |
| 4,560,552 A | 12/1985 | Cole et al. | |
| 4,568,741 A | 2/1986 | Livingston | |
| 4,598,045 A | 7/1986 | Masover et al. | |
| 4,616,008 A | 10/1986 | Hirai et al. | |
| 4,634,697 A | 1/1987 | Hamashima | |
| 4,644,031 A | 2/1987 | Lehmann et al. | |
| 4,670,549 A | 6/1987 | Morimoto et al. | |
| 4,672,109 A | 6/1987 | Watanabe et al. | |
| 4,680,386 A | 7/1987 | Morimoto et al. | |
| 4,710,565 A | 12/1987 | Livingston et al. | |
| 4,723,958 A | 2/1988 | Pope et al. | |
| 4,728,512 A | 3/1988 | Mehta et al. | |
| 4,749,568 A | 6/1988 | Reusser et al. | |
| 4,755,385 A | 7/1988 | Etienne et al. | |
| 4,775,751 A | 10/1988 | McShane | |
| 4,794,001 A | 12/1988 | Mehta et al. | |
| 4,808,411 A | 2/1989 | Lu et al. | |
| 4,812,561 A | 3/1989 | Hamashima et al. | |
| 4,828,836 A | 5/1989 | Elger et al. | |
| 4,831,025 A | 5/1989 | Godtfredsen et al. | |
| 4,835,140 A | 5/1989 | Smith et al. | |
| 4,842,866 A | 6/1989 | Horder et al. | |
| 4,849,515 A | 7/1989 | Matier et al. | |
| 4,879,135 A | 11/1989 | Greco et al. | |
| 4,894,119 A | 1/1990 | Baron, Jr. et al. | |
| 4,895,934 A | 1/1990 | Matier et al. | |
| 4,904,476 A | 2/1990 | Mehta et al. | |
| 4,915,953 A | 4/1990 | Jordan et al. | |
| 4,945,080 A | 7/1990 | Lindstrom et al. | |
| 4,945,405 A | 7/1990 | Hirota | |
| 4,971,805 A | 11/1990 | Kitanishi et al. | |
| 4,990,602 A | 2/1991 | Morimoto et al. | |

(Continued)

FOREIGN PATENT DOCUMENTS

| | | |
|---|---|---|
| EP | 0052075 | 11/1981 |
| EP | 0293885 | 12/1988 |

(Continued)

OTHER PUBLICATIONS

Mainz et al "Pharmacokinetics of lansoprazole, amoxicillin and clarithromycin after simultaneous and single administration," Journal of Antimicrobial Chemotherapy (2000) 50, 699-706.*

(Continued)

*Primary Examiner* — Suzanne Ziska

(74) *Attorney, Agent, or Firm* — MH2 Technology Law Group, LLP

(57) ABSTRACT

An amoxicillin product comprising: at least one modified release component(s), wherein the at least one modified release component(s) comprises at least amoxicillin and a pharmaceutically acceptable carrier; and wherein when administered to a patient or subject in the fed state said amoxicillin product exhibits a pharmacokinetic profile for amoxicillin in the plasma characterized as follows: (1) the ratio of the portion of the AUC as measured from 2 hours post-administration to 5 hours post-administration to the portion of the AUC as measured from administration to 2 hours post-administration is at least 2.0:1; and (2) the ratio of the portion of the AUC as measured from 5 hours post-administration to 12 hours post-administration to the portion of the AUC as measured from administration to 2 hours post-administration is at least 1.1:1.

60 Claims, No Drawings

(56) References Cited

U.S. PATENT DOCUMENTS

| | | |
|---|---|---|
| 5,011,692 A | 4/1991 | Fujiota et al. |
| 5,045,533 A | 9/1991 | Philippe et al. |
| 5,051,262 A | 9/1991 | Panoz et al. |
| 5,110,597 A | 5/1992 | Wong et al. |
| 5,110,598 A | 5/1992 | Kwan et al. |
| 5,143,661 A | 9/1992 | Lawter et al. |
| 5,158,777 A | 10/1992 | Abramowitz et al. |
| 5,178,874 A | 1/1993 | Kwan et al. |
| 5,182,374 A | 1/1993 | Tobkes et al. |
| 5,200,193 A | 4/1993 | Radebaugh et al. |
| 5,204,055 A | 4/1993 | Sachs et al. |
| 5,213,808 A | 5/1993 | Bar-Shalom et al. |
| 5,229,131 A | 7/1993 | Amidon et al. |
| 5,230,703 A | 7/1993 | Alon |
| 5,274,085 A | 12/1993 | Amano et al. |
| 5,288,503 A | 2/1994 | Wood et al. |
| 5,334,590 A | 8/1994 | DiNinno et al. |
| 5,340,656 A | 8/1994 | Sachs et al. |
| 5,358,713 A | 10/1994 | Shimamura |
| 5,387,380 A | 2/1995 | Cima et al. |
| 5,393,765 A | 2/1995 | Infeld et al. |
| 5,395,626 A | 3/1995 | Kotwal et al. |
| 5,395,628 A | 3/1995 | Noda et al. |
| 5,399,723 A | 3/1995 | Iinuma et al. |
| 5,401,512 A | 3/1995 | Rhodes et al. |
| 5,407,686 A | 4/1995 | Patel et al. |
| 5,413,777 A | 5/1995 | Sheth et al. |
| 5,414,014 A | 5/1995 | Schneider et al. |
| 5,422,343 A | 6/1995 | Yamamoto et al. |
| 5,430,021 A | 7/1995 | Rudnic et al. |
| 5,445,829 A | 8/1995 | Paradissis et al. |
| 5,457,187 A | 10/1995 | Gmeiner et al. |
| 5,462,747 A | 10/1995 | Radebaugh et al. |
| 5,466,446 A | 11/1995 | Stiefel et al. |
| 5,472,708 A | 12/1995 | Chen |
| 5,476,854 A | 12/1995 | Young |
| 5,490,962 A | 2/1996 | Cima et al. |
| 5,508,040 A | 4/1996 | Chen |
| 5,518,680 A | 5/1996 | Cima et al. |
| 5,538,954 A | 7/1996 | Koch et al. |
| 5,543,417 A | 8/1996 | Waldstreicher |
| 5,556,839 A | 9/1996 | Greene et al. |
| 5,567,441 A | 10/1996 | Chen |
| 5,576,022 A | 11/1996 | Yang et al. |
| 5,578,713 A | 11/1996 | McGill, III |
| 5,599,557 A | 2/1997 | Johnson et al. |
| 5,607,685 A | 3/1997 | Cimbollek et al. |
| 5,633,006 A | 5/1997 | Catania et al. |
| 5,672,359 A | 9/1997 | Digenis et al. |
| 5,688,516 A | 11/1997 | Raad et al. |
| 5,702,895 A | 12/1997 | Matsunaga et al. |
| 5,705,190 A | 1/1998 | Broad et al. |
| 5,707,646 A | 1/1998 | Yajima et al. |
| 5,719,132 A | 2/1998 | Lin et al. |
| 5,719,272 A | 2/1998 | Yang et al. |
| 5,725,553 A | 3/1998 | Moenning |
| 5,733,886 A | 3/1998 | Baroody et al. |
| 5,756,473 A | 5/1998 | Liu et al. |
| 5,780,446 A | 7/1998 | Ramu |
| 5,789,584 A | 8/1998 | Christensen et al. |
| 5,808,017 A | 9/1998 | Chang |
| 5,817,321 A | 10/1998 | Alakhov et al. |
| 5,827,531 A | 10/1998 | Morrison et al. |
| 5,837,284 A | 11/1998 | Mehta et al. |
| 5,837,829 A | 11/1998 | Ku |
| 5,840,329 A | 11/1998 | Bai |
| 5,840,760 A | 11/1998 | Carraher, Jr. et al. |
| 5,844,105 A | 12/1998 | Liu et al. |
| 5,849,776 A | 12/1998 | Czernielewski et al. |
| 5,852,180 A | 12/1998 | Patel |
| 5,858,986 A | 1/1999 | Liu et al. |
| 5,864,023 A | 1/1999 | Ku et al. |
| 5,869,170 A | 2/1999 | Cima et al. |
| 5,872,104 A | 2/1999 | Vermeulen et al. |
| 5,872,229 A | 2/1999 | Liu et al. |
| 5,877,243 A | 3/1999 | Sarangapani |
| 5,883,079 A | 3/1999 | Zopf et al. |
| 5,892,008 A | 4/1999 | Ku et al. |
| 5,910,322 A | 6/1999 | Rivett et al. |
| 5,919,219 A | 7/1999 | Knowlton |
| 5,919,489 A | 7/1999 | Saleki-Gerhardt et al. |
| 5,919,916 A | 7/1999 | Gracey et al. |
| 5,929,219 A | 7/1999 | Hill |
| 5,932,710 A | 8/1999 | Liu et al. |
| 5,945,124 A | 8/1999 | Sachs et al. |
| 5,945,405 A | 8/1999 | Spanton et al. |
| 5,972,373 A | 10/1999 | Yajima et al. |
| 5,980,942 A | 11/1999 | Katzhendler et al. |
| 5,985,643 A | 11/1999 | Tomasz et al. |
| 5,998,194 A | 12/1999 | Summers, Jr. et al. |
| 6,008,195 A | 12/1999 | Selsted |
| 6,010,718 A | 1/2000 | Al-Razzak et al. |
| 6,013,507 A | 1/2000 | Tomasz et al. |
| 6,027,748 A | 2/2000 | Conte et al. |
| 6,031,093 A | 2/2000 | Cole et al. |
| 6,048,977 A | 4/2000 | Cole et al. |
| 6,051,255 A | 4/2000 | Conley et al. |
| 6,051,703 A | 4/2000 | Cole et al. |
| 6,057,291 A | 5/2000 | Hancock et al. |
| 6,059,816 A | 5/2000 | Moenning |
| 6,063,613 A | 5/2000 | De Lencastre et al. |
| 6,063,917 A | 5/2000 | Ascher et al. |
| 6,068,859 A | 5/2000 | Curatolo et al. |
| 6,110,925 A | 8/2000 | Williams et al. |
| 6,117,843 A | 9/2000 | Baroody et al. |
| 6,120,803 A | 9/2000 | Wong et al. |
| 6,127,349 A | 10/2000 | Chasalow |
| 6,132,768 A | 10/2000 | Sachs et al. |
| 6,132,771 A | 10/2000 | Depui et al. |
| 6,136,587 A | 10/2000 | Tomasz et al. |
| 6,156,507 A | 12/2000 | Hiramatsu et al. |
| 6,159,491 A | 12/2000 | Durrani |
| 6,162,925 A | 12/2000 | Williams et al. |
| 6,183,778 B1 | 2/2001 | Conte et al. |
| 6,187,768 B1 | 2/2001 | Welle et al. |
| 6,214,359 B1 | 4/2001 | Bax |
| 6,218,380 B1 | 4/2001 | Cole et al. |
| 6,228,398 B1 | 5/2001 | Devane et al. |
| 6,231,875 B1 | 5/2001 | Sun et al. |
| 6,248,363 B1 | 6/2001 | Patel et al. |
| 6,251,647 B1 | 6/2001 | De Lencastre et al. |
| 6,265,394 B1 | 7/2001 | Sterzycki et al. |
| 6,270,805 B1 | 8/2001 | Chen et al. |
| 6,280,771 B1 | 8/2001 | Monkhouse et al. |
| 6,294,199 B1 | 9/2001 | Conley et al. |
| 6,294,526 B1 | 9/2001 | Higuchi et al. |
| 6,296,873 B1 | 10/2001 | Katzhendler et al. |
| 6,297,215 B1 | 10/2001 | Hancock et al. |
| 6,299,903 B1 | 10/2001 | Rivett et al. |
| 6,306,436 B1 | 10/2001 | Chungi et al. |
| 6,309,663 B1 | 10/2001 | Patel et al. |
| 6,322,819 B1 | 11/2001 | Burnside et al. |
| 6,333,050 B2 | 12/2001 | Wong et al. |
| 6,340,475 B2 | 1/2002 | Shell et al. |
| 6,352,720 B1 | 3/2002 | Martin et al. |
| 6,358,525 B1 | 3/2002 | Guo et al. |
| 6,358,528 B1 | 3/2002 | Grimmett et al. |
| 6,383,471 B1 | 5/2002 | Chen et al. |
| 6,384,081 B2 | 5/2002 | Berman |
| 6,391,614 B1 | 5/2002 | Tomasz et al. |
| 6,399,086 B1 | 6/2002 | Katzhendler et al. |
| 6,403,569 B1 | 6/2002 | Achterrath |
| 6,406,717 B2 | 6/2002 | Cherukuri |
| 6,406,880 B1 | 6/2002 | Thornton |
| 6,440,462 B1 | 8/2002 | Raneburger et al. |
| 6,444,796 B1 | 9/2002 | Suh et al. |
| 6,468,964 B1 | 10/2002 | Rowe |
| 6,479,496 B1 | 11/2002 | Wolff |
| 6,495,157 B1 | 12/2002 | Pena et al. |
| 6,497,901 B1 | 12/2002 | Royer |
| 6,503,709 B1 | 1/2003 | Bekkaoui et al. |
| 6,508,886 B1 | 1/2003 | Lee et al. |
| 6,514,518 B2 | 2/2003 | Monkhouse et al. |
| 6,515,010 B1 | 2/2003 | Franchini et al. |

(56) References Cited

U.S. PATENT DOCUMENTS

| | | |
|---|---|---|
| 6,515,116 B2 | 2/2003 | Suh et al. |
| 6,530,958 B1 | 3/2003 | Cima et al. |
| 6,541,014 B2 | 4/2003 | Rudnic et al. |
| 6,544,555 B2 | 4/2003 | Rudnic et al. |
| 6,548,084 B2 | 4/2003 | Leonard et al. |
| 6,550,955 B2 | 4/2003 | D'Silva |
| 6,551,584 B2 | 4/2003 | Bandyopadhyay et al. |
| 6,551,616 B1 | 4/2003 | Notario et al. |
| 6,558,699 B2 | 5/2003 | Venkatesh |
| 6,565,873 B1 | 5/2003 | Shefer et al. |
| 6,565,882 B2 | 5/2003 | Rudnic |
| 6,569,463 B2 | 5/2003 | Patel et al. |
| 6,585,997 B2 | 7/2003 | Moro et al. |
| 6,599,884 B2 | 7/2003 | Avrutov et al. |
| 6,605,069 B1 | 8/2003 | Albers et al. |
| 6,605,300 B1 | 8/2003 | Burnside et al. |
| 6,605,609 B2 | 8/2003 | Barbachyn et al. |
| 6,605,751 B1 | 8/2003 | Gibbins et al. |
| 6,610,323 B1 | 8/2003 | Lundberg et al. |
| 6,610,328 B2 | 8/2003 | Rudnic et al. |
| 6,617,436 B2 | 9/2003 | Avrutov et al. |
| 6,623,757 B2 | 9/2003 | Rudnic et al. |
| 6,623,758 B2 | 9/2003 | Rudnic et al. |
| 6,624,292 B2 | 9/2003 | Lifshitz et al. |
| 6,627,222 B2 | 9/2003 | Rudnic et al. |
| 6,627,743 B1 | 9/2003 | Liu et al. |
| 6,630,498 B2 | 10/2003 | Gudipati et al. |
| 6,632,453 B2 | 10/2003 | Rudnic et al. |
| 6,635,280 B2 | 10/2003 | Shell et al. |
| 6,638,532 B2 | 10/2003 | Rudnic et al. |
| 6,642,276 B2 | 11/2003 | Wadhwa |
| 6,663,890 B2 | 12/2003 | Rudnic et al. |
| 6,663,891 B2 | 12/2003 | Rudnic et al. |
| 6,667,042 B2 | 12/2003 | Rudnic et al. |
| 6,667,057 B2 | 12/2003 | Rudnic et al. |
| 6,669,948 B2 * | 12/2003 | Rudnic et al. ............... 424/400 |
| 6,669,955 B2 | 12/2003 | Chungi et al. |
| 6,673,369 B2 | 1/2004 | Rampal et al. |
| 6,682,759 B2 | 1/2004 | Lim et al. |
| 6,698,426 B1 | 3/2004 | Singh et al. |
| 6,702,803 B2 | 3/2004 | Kupperblatt et al. |
| 6,706,273 B1 | 3/2004 | Roessler |
| 6,723,340 B2 | 4/2004 | Gusler et al. |
| 6,723,341 B2 | 4/2004 | Rudnic et al. |
| 6,730,320 B2 | 5/2004 | Rudnic et al. |
| 6,730,325 B2 | 5/2004 | Devane et al. |
| 6,735,470 B2 | 5/2004 | Henley et al. |
| 6,740,664 B2 | 5/2004 | Cagle et al. |
| 6,746,692 B2 | 6/2004 | Conley et al. |
| 6,756,057 B2 | 6/2004 | Storm et al. |
| 6,767,899 B1 | 7/2004 | Kay et al. |
| 6,777,420 B2 | 8/2004 | Zhi et al. |
| 6,783,773 B1 | 8/2004 | Storm et al. |
| 6,818,407 B2 | 11/2004 | Hancock et al. |
| 6,824,792 B2 | 11/2004 | Foreman et al. |
| 6,872,407 B2 | 3/2005 | Notario et al. |
| 6,878,386 B1 | 4/2005 | Conley et al. |
| 6,878,387 B1 | 4/2005 | Petereit et al. |
| 6,906,035 B2 | 6/2005 | Hancock et al. |
| 6,929,804 B2 | 8/2005 | Rudnic et al. |
| 6,946,458 B2 | 9/2005 | Turos |
| 6,984,401 B2 | 1/2006 | Rudnic et al. |
| 6,991,807 B2 | 1/2006 | Rudnic et al. |
| 7,008,633 B2 | 3/2006 | Yang et al. |
| 7,025,989 B2 | 4/2006 | Rudnic et al. |
| 2001/0046984 A1 | 11/2001 | Rudnic |
| 2001/0048944 A1 * | 12/2001 | Rudnic et al. ............... 424/468 |
| 2002/0004070 A1 | 1/2002 | Rudnic et al. |
| 2002/0004499 A1 | 1/2002 | Rudnic et al. |
| 2002/0015728 A1 | 2/2002 | Payumo et al. |
| 2002/0028920 A1 | 3/2002 | Lifshitz et al. |
| 2002/0042394 A1 | 4/2002 | Hogenkamp et al. |
| 2002/0068078 A1 | 6/2002 | Rudnic et al. |
| 2002/0068085 A1 | 6/2002 | Rudnic et al. |
| 2002/0081332 A1 | 6/2002 | Rampal et al. |
| 2002/0103261 A1 | 8/2002 | Ninkov |
| 2002/0106412 A1 | 8/2002 | Rowe et al. |
| 2002/0115624 A1 | 8/2002 | Behar et al. |
| 2002/0119168 A1 | 8/2002 | Rudnic et al. |
| 2002/0136764 A1 | 9/2002 | Rudnic et al. |
| 2002/0136765 A1 | 9/2002 | Rudnic et al. |
| 2002/0136766 A1 | 9/2002 | Rudnic et al. |
| 2002/0150619 A1 | 10/2002 | Rudnic et al. |
| 2002/0197314 A1 | 12/2002 | Rudnic et al. |
| 2003/0012814 A1 | 1/2003 | Rudnic et al. |
| 2003/0018295 A1 | 1/2003 | Henley et al. |
| 2003/0044465 A1 | 3/2003 | Yasuura et al. |
| 2003/0049311 A1 | 3/2003 | McAllister et al. |
| 2003/0064100 A1 | 4/2003 | Rudnic et al. |
| 2003/0073647 A1 | 4/2003 | Chao et al. |
| 2003/0073648 A1 | 4/2003 | Chao et al. |
| 2003/0073826 A1 | 4/2003 | Chao et al. |
| 2003/0077323 A1 | 4/2003 | Rudnic et al. |
| 2003/0086969 A1 | 5/2003 | Rudnic et al. |
| 2003/0091627 A1 | 5/2003 | Sharma |
| 2003/0096006 A1 | 5/2003 | Rudnic et al. |
| 2003/0096007 A1 | 5/2003 | Rudnic et al. |
| 2003/0096008 A1 | 5/2003 | Rudnic et al. |
| 2003/0099706 A1 | 5/2003 | Rudnic et al. |
| 2003/0099707 A1 | 5/2003 | Rudnic et al. |
| 2003/0104054 A1 | 6/2003 | Rudnic et al. |
| 2003/0104055 A1 | 6/2003 | Rudnic et al. |
| 2003/0104056 A1 | 6/2003 | Rudnic et al. |
| 2003/0104058 A1 | 6/2003 | Rudnic et al. |
| 2003/0124196 A1 | 7/2003 | Weinbach et al. |
| 2003/0129236 A1 | 7/2003 | Heimlich et al. |
| 2003/0143268 A1 | 7/2003 | Pryce Lewis et al. |
| 2003/0147953 A1 | 8/2003 | Rudnic et al. |
| 2003/0190360 A1 | 10/2003 | Baichwal et al. |
| 2003/0198677 A1 | 10/2003 | Pryce Lewis et al. |
| 2003/0199808 A1 | 10/2003 | Henley et al. |
| 2003/0203023 A1 | 10/2003 | Rudnic et al. |
| 2003/0206951 A1 | 11/2003 | Rudnic et al. |
| 2003/0216555 A1 | 11/2003 | Lifshitz et al. |
| 2003/0216556 A1 | 11/2003 | Avrutov et al. |
| 2003/0232082 A1 | 12/2003 | Li et al. |
| 2003/0232089 A1 | 12/2003 | Singh et al. |
| 2003/0235615 A1 | 12/2003 | Rudnic |
| 2004/0018234 A1 | 1/2004 | Rudnic et al. |
| 2004/0033262 A1 | 2/2004 | Kshirsagar et al. |
| 2004/0043073 A1 | 3/2004 | Chen et al. |
| 2004/0047906 A1 | 3/2004 | Percel et al. |
| 2004/0048814 A1 | 3/2004 | Rudnic et al. |
| 2004/0052842 A1 | 3/2004 | Rudnic et al. |
| 2004/0058879 A1 | 3/2004 | Avrutov et al. |
| 2004/0091528 A1 | 5/2004 | Rogers et al. |
| 2004/0126427 A1 | 7/2004 | Venkatesh et al. |
| 2004/0176737 A1 | 9/2004 | Henley et al. |
| 2004/0208936 A1 * | 10/2004 | Chorin et al. ............... 424/490 |
| 2004/0219223 A1 | 11/2004 | Kunz |
| 2004/0241172 A1 | 12/2004 | Axworthy et al. |
| 2004/0253249 A1 | 12/2004 | Rudnic et al. |
| 2004/0265379 A1 | 12/2004 | Conley et al. |
| 2005/0019401 A1 | 1/2005 | Burnside et al. |
| 2005/0019402 A1 | 1/2005 | Burnside et al. |
| 2005/0019403 A1 * | 1/2005 | Burnside et al. ............... 424/468 |
| 2005/0053658 A1 | 3/2005 | Venkatesh et al. |
| 2005/0064033 A1 | 3/2005 | Notario et al. |
| 2005/0064034 A1 | 3/2005 | Li et al. |
| 2005/0142187 A1 * | 6/2005 | Treacy et al. ............... 424/451 |
| 2005/0163857 A1 | 7/2005 | Rampal et al. |
| 2005/0203076 A1 | 9/2005 | Li et al. |
| 2005/0203085 A1 | 9/2005 | Li et al. |
| 2005/0209210 A1 | 9/2005 | Ding et al. |
| 2005/0238714 A1 | 10/2005 | Rudnic et al. |
| 2005/0256096 A1 | 11/2005 | Combrink et al. |
| 2005/0261262 A1 | 11/2005 | Ma et al. |
| 2005/0277633 A1 | 12/2005 | Ma et al. |
| 2006/0003005 A1 | 1/2006 | Cao et al. |
| 2006/0019985 A1 | 1/2006 | Ma et al. |
| 2006/0019986 A1 | 1/2006 | Ding et al. |
| 2006/0111302 A1 | 5/2006 | Romesberg et al. |
| 2006/0194748 A1 | 8/2006 | Minami et al. |
| 2008/0026056 A1 | 1/2008 | Guimberteau et al. |

(56) References Cited

U.S. PATENT DOCUMENTS

| | | |
|---|---|---|
| 2008/0050430 A1 | 2/2008 | Flanner et al. |
| 2008/0132478 A1 | 6/2008 | Flanner et al. |
| 2008/0139526 A1 | 6/2008 | Treacy et al. |

FOREIGN PATENT DOCUMENTS

| | | |
|---|---|---|
| EP | 0 312 581 | 4/1989 |
| EP | 0436370 | 7/1991 |
| EP | 0652008 | 5/1995 |
| FR | 2585948 | 2/1982 |
| GB | 2087235 | 5/1982 |
| JP | 2008-157392 | 6/1996 |
| WO | 90/08537 | 8/1990 |
| WO | 94/27557 | 12/1994 |
| WO | 95/20946 | 8/1995 |
| WO | 95/30422 | 11/1995 |
| WO | 96/04908 | 2/1996 |
| WO | 97/22335 | 6/1997 |
| WO | 97/43277 | 11/1997 |
| WO | 98/22091 | 5/1998 |
| WO | 98/46239 | 10/1998 |
| WO | 99/03453 | 1/1999 |
| WO | 99/40097 | 8/1999 |
| WO | 00/48607 | 8/2000 |
| WO | 00/61115 | 10/2000 |
| WO | 00/61116 | 10/2000 |
| WO | 01/26663 | 4/2001 |
| WO | 0162229 | 8/2001 |
| WO | 02/38577 | 5/2002 |
| WO | 03/029439 | 4/2003 |
| WO | 03/086344 A1 | 10/2003 |
| WO | 2005/009368 | 2/2005 |
| WO | 2005030178 | 4/2005 |
| WO | 2005/056754 | 6/2005 |
| WO | 2005/062898 | 7/2005 |
| WO | 2005/070941 | 8/2005 |
| WO | 2005/099672 | 10/2005 |

OTHER PUBLICATIONS

Chhipa et al "Formulation Optimization of Sustained Release Pellets of Itopride Hydrochloride using Different Polymers," Journal of Pharmacy Research 2009 2(8) 1404-1408.*
Mainz et al ("Pharmacokinetics of lansoprazole, amoxicillin and clarithromycin after simultaneous and single administration," Journal of Antimicrobial Chemotherapy (2000) 50, 699-706).*
Hilton et al ("Use of Hydroxypropyl Methylcellulose Acetate Succinate in an Enteric Polymer Matrix to Design Controlled-Release Tablets of Amoxicillin Trihydrate," Journal of pharmaceutical Sciences vol. 82, No. 7, Jul. 1993 pp. 737-743).*
English Translation of Office Action dated Jul. 3, 2012 from Japanese Patent Application No. 2009-539226, 4 pages.
English Translation of Japanese Office Action mailed Dec. 11, 2012 in Japanese Patent Application No. 2009-539226.
Bahnmuller, Metabolites of Microorganisms, 248, Synthetic Analogs of Saphenamycin, J. Antibiot. (Tokyo). Nov. 1988; 41(11): 1552-60.
Borman, Chemistry Highlights 2005, Chemical & Engineering News, Dec. 19, 2005, vol. 83, No. 51, pp. 15-20.
Bradley, *Staphylococcus aureus* Pneumonia: Emergence of MRSA in the Community, Semin Respir Crit Care Med. 2005; 26(6): 643-649.
Cirz, et al., Inhibition of Mutation and Combating the Evolution of Antibiotic Resistance, PLOS Biology, Jun. 2005, vol. 3, Issue 6, e176, pp. 1024-1033.
Darst, New Inhibitors Targeting Bacterial RNA Polymerase, Trends in Biochemical Sciences, vol. 29, No. 4, Apr. 2004, pp. 159-162.
Dellit, M.D., Tim, University of Washington and Infectious Diseases Society of Washington; Jeffrey Duchin, MD, Public Health—Seattle & King County and University of Washington; Jo Hofmann, MD, Washington State Department of Health and University of of Washington; Erika Gumai Olson, MD, Tacome-Pierce County Health Department Antibiotic Resistance Task Force, Interim Guidelines for Evaluation and Management of Community-Associated Methicillin-Resistant *Staphylococcus aureus* Skin and Soft Tissue Infections in Outpatient Settings, Sep. 2, 2004.
Geiger et al., Metabolites of Microorganisms. 247, Phenazines from *Streptomyces antibioticus*, Strain Tu 2706, J Antibiot (Tokyo), Nov. 1988; 41(11): 1542-51.
Gorwitz et al., Strategies for Clinical Management of MRSA in the Community: Summary of an Expert's Meeting Convened by the Centers for Disease Control and Prevention, Department of Health and Human Services Centers for Disease Control and Prevention, Mar. 2006.
Henry, Disabling Resistance Inhibiting Key Protease Prevents Bacteria From Evolving Drug Resistance, Chemical and Engineering News, May 16, 2006, vol. 83, No. 20, p. 8.
Johnson, N. J. Experts Urge Prudent Antibiotic Use, Examiner.Com, The Associated Press, Jul. 31, 2006.
Kitahara et al., Saphenamycin, A Novel Antibiotic From a Strain of *Streptomyces*, J Antibiot (Tokyo). Oct. 1982; 35 (10): 1412-4.
Laursen et al., Solid-Phase Synthesis of New Saphenamycin Analogues with Antimicrobial Activity, Bioorg. Med. Chem. Lett. Jan. 21, 2002: 12(2): 171-5.
Laursen et al., First Synthesis of Racemic Saphenamycin and Its Enantiomers. Investigation of Biological Activity, Bioorg. Med. Chem. Mar. 6, 2003: 11(5): 723-31.
Laursen et al., Efficient Synthesis of Glycosylated Phenazine Natural Products and Analogs with DISAL (Methyl 3, 5-Dinitrosalicylate) Glycosyl Donors, Org. Biomol. Chem. Sep. 21, 2003; 1(18): 3147-53.
Reusser, Inhibition of Ribosomal and RNA Polymerase Functions by Rubradirin and Its Aglycone, J Antibiot (Tokyo) Nov. 1979; 32(11): 1186-92.
Rihn, et al., Community-Acquired Methicillin-Resistant *Staphylococcus aureus*: An Emerging Problem in the Athletic Population, AM J Sports Med. Dec. 2005; 33(12): 1924-9.
Salmenlinna et al., Community-Acquired Methicillin-Resistant *Staphylococcus aureus*, Finland, Emerg. Infect. Dis. Jun. 2002; 8(6): 602-7.
Vandenesch et al., Community-Acquired Methicillin-Resistant *Staphylococcus aureus* Carrying Panton-Valentine Leukocidin Genes:Worldwide Emergence, Emerg. Infect. Dis. Aug. 2003; 9(8): 978-84.
Can We Prevent Bacteria From Developing Resistance to Antibiotics?, Sep. 2005, AAPS News Magazine 15.
Healthcare-Associated Methicillin Resistant *Staphylococcus aureus* (HA-MRSA), Department of Health and Human Services, Centers for Disease Control and Prevention, Jun. 1, 2005.
Methicillin-Resistant *Staphylococcus aureus*, HealthLink, Medical College of Wisconsin, Information Provided by the Wisconsin Department of Health and Human Services, Article Reviewed: Apr. 10, 2000, 2003 Medical College of Wisconsin.
Methicillin-Resistant *Staphylococcus aureus* (MRSA) Infection, Written by Dr. Alan Johnson, Clinical Scientist, Webiste: www.mrsasupport.co.uk, Jan. 8, 2005.
The Public's Health, Back-To-School: Review Immunization Records Early, What Doctors and Parents Need to Know About Immunizations and School, vol. 5, No. 7, Jul.-Aug. 2005.
Sulfenamide Class Antibiotics, ChemicalLand21.com.
Adjei et al., Comparative Pharmacokinetic Study of Continuous Venous Infusion Fluorouracil and Oral Fluorouracil With Eniluracil in Patients with Advanced Solid Tumors, Journal of Clinical Oncology, vol. 20, Issue 6 Mar. 2002, 1686-19691.
Andes, Pharmacokinetic and Pharmacodynamic Properties of Antimicrobials in the Therapy of Respiratory Tract Infections, Current Opinion in Infectious Diseases, 14(2):165-172, Apr. 2001. (Abstract).
Auckenthaler, Pharmacokinetics and Pharmacodynamics of Oral Beta-Lactam Antibiotics as a Two-Dimensional Approach to Their Efficacy, J Antimicrob Chemother, (2002) 50, 13-17.
Berry et al., Bacteriological Efficacies of Three Macrolides Compared with Those Amoxicillin-Clavulanate Against *Streptococcus pneumoniae* Influenzae, Antimicrob Agents Chemother. Dec. 1998 42(12): 3193-3199.

(56) References Cited

OTHER PUBLICATIONS

Bhargava et al., Pulsed Feeding During Fed-Batch Fungal Fermentation Leads to Reduced Viscosity Without Detrimentally Affecting Protein Expression, Biotechnology and Bioengineering, vol. 81, No. 3, Feb. 5, 2003, pp. 341-347.
Bhargava et al., Pulsed Feeding During Fed-Batch *Aspergillus oryzae* Fermentation Leads to improved Oxygen Mass Transfer, Biotechnol. Prog. 2003, 19, 1091-1094.
Bhargava et al., Pulsed Addition of Limiting-Carbon During *Aspergillus oryzae* Fermentation Leads to Improved Productivity of a Recombinant Enzyme, Biotechnology and Bioengineering, vol. 82, No. 1, Apr. 5, 2003, pp. 111-117.
Bishai, Comparative Effectiveness of Different Macrolides: Clarithromycin, Azithromycin, and Erythromycin, Johns Hopkins Point of Care information Technology (POC-IT), posted Dec. 2001.
Bradley, *Staphylococcus aureus* Pneumonia: Emergence of MRSA in the Community, Semin Respir Crit Care Med. 2005; 28(6): 643-649.
Brogden et al., Cefixime. A Revew of Its Antibacterial Activity. Pharmacokinetic Properties and Therapeutic Potential, Drugs, Oct. 1989; 38(4): 524-50. (Abstract).
Burgess et al., A Time-Kill Evaluation of Clarithromycin and Azithromycin Against Two Extracellular Pathogens and the Development of Resistance, The Annals of Pharmacotherapy: 1999, vol. 33, No. 12, pp. 1262-1265 (Abstract).
Byfield et al., Relevance of the Pharmacology of Oral Tegafur to its Use as a 5-FU Pro-Drug., Cancer Treat Rep. Jun. 1985; 69 (6): 645-52. (Abstract).
Cappelletty et al., Bactericidal Activities of Cefprozil, Penicillin, Cefaclor, Cefixime, and Loracarbef against Penicillin-Susceptible and Resistant *Streptococcus pneumoniae* in an In Vitro Pharamcodynamic Infection Model, Antimicrobial Agents and Chemotherapy, May 1996, p. 1148-1152.
Cha et al., Pulsatile Delivery of Amoxicillin Against *Streptococcus pneumoniae*, Journal of Antimicrobial Chemotherapy, Advance Access Published Oct. 14, 2004.
Craig, Antibiotic Selection Factors and Description of a Hospital-Based Outpatient Antibiotic Therapy Program in the USA, Eur J Clin Microbiol Infect Dis. Jul. 1995; 14(7): 636-42. (Abstract).
Cremieux et al., Ceftriaxone Diffusion into Cardiac Fibrin Vegetation. Qualitative and Quantitative Evaluation by Autoradiography, Fundam Clin Pharamcol. 1991; 5(1);53-60. (Abstract).
Endo et al., Fungicidal Action of Aureobasidin A, a Cyclic Depsipeptide Antifungal Antibiotic, against *Saccharomyces cerevisiae*, Antimicrobial Agents and Chemotherapy, Mar. 1997, p. 672-676.
Erah et al., The Stability of Amoxycillin, Clarithromycin and Metronidazole in Gastric Juice: Relevance to the Treatment of *Helicobacter pylori* Infection, J Antimicrob Chemother Jan. 1997; 39(1):5-12, (Abstract).
Fang, A Study of the Ethical Considerations and Implications, Prozac, Weekly and Sarafem in the Wake of Prozac Patent Expiration, 5.22J/10.02J, Biotechnology and Engineering, 2002.
Feder et al. Once-Daily Therapy far *Streptococcal pharyngitis* With Amoxicillin, American Academy of Pediatrics, vol. 103(1), Jan. 1999, pp. 47-51.
Freeman et al., The Cyclosporin-Erythromycin Interaction: Impaired First Pass Metabolism in the Pig, Br J Pharmacol. Jul. 1991; 103(3): 1709-12, (Abstract).
Frimodt-Moller, Correlation Between Pharmacokinectic / Pharmacodynamic Parameters and Efficacy for Antibiotics in the Treatment of Urinary Tract Infection, Int. J. Antimicrob. Agents, 19 (2002) 546-53.
Furlanut et al., Pharmacokinetic Aspects of Levofloxacin 500mg Once Daily During Sequential Intravenous/Oral Therapy in Patients with Lower Respiratory Tract Infections, Journal of Antimicrobial Chemotherapy (2002) 51, 101-106.
Gill et al., In Vivo Activity and Pharmacokinetic Evaluation of a Novel Long-Acting Carbapenem Antibiotic, MK-826 (L-749, 345), Antimicrobial Agents and Chemotherapy, Aug. 1998; 42(8):1996-2001.
Gnarpe et al., Penicillin Combinations Against Multi-Resistant Urinary Pathogens as an Alternative to Gentamycin Treatment, Microbios 1976: 16(65-66):201-6. (Abstract).
Gordon et al., Rationale for Single and High Dose Treatment Regiments with Azithromycin, Pediatric Infectious Disease Journal. 23(2) Supplement: S102-S107, Feb. 2004. (Abstract).
Goswick et al., Activities of Azithromycin and Amphotericin B Against *Naegleria fowleri* in Vitro and in a Mouse Model of Primary Amebic Meningoencephalitis, Antimicrob Agents Chemother. Feb. 2003; 47(2): 524-628.
Harbath et al., Prolonged Antibiotic Prophylaxis After Cardiovascular Surgery and Its Effect on Surgical Site Infections and Antimicrobial Resistance, Circulation Jun. 27, 2000; 101:2916-2921.
Haney, New Drugs Kill Bacteria Resistant to Antibiotics, Called Ketolides, They are Chemically New to the Harmful Bugs, Thursday, Sep. 21, 2000, Seattle Post-Intelligencer.
Harris et al., Esophageal Carcinoma: Curative Treatment, Combined Modalities, The Virtual Hospital, 2004.
Hickey et al., Production of Enterolysin A by a Raw Milk Enterococcal Isolate Exhibiting Multiple Virulence Factors, Microbiology 149 (2003), 655-664.
Hirata et al., Pharmacokinetic Study of S-1, a Novel Oral Fluorouracil Antitumor Drug, Clinical Cancer Research vol. 5, 2000-2005, Aug. 1999.
Hoff et al., Phase I Study with Pharmacokinetics of S-1 on an Oral Daily Schedule for 28 Days in Patients with Solid Tumors, Clinical Cancer Research vol. 9, 134-142, Jan. 2003.
Hoffman et al., Pharmacodynamic and Pharmacokinetic Rationales for the Development of an Oral Controlled-Release Amoxicillin Dosage Form, Journal of Controlled Release 54 (1988) 29-37.
Hoffmann et al., Influence of Macrolide Susceptibility of Efficacies of Clarithromycin and Azithromycin Against *Strepotococcus pneumoniae* in a Murine Lung Infection Model, Antimicrobial Agents and Chemotherapy, Feb. 2003, p. 739-746, vol. 47, No. 2.
Hyde et al., Macrolide Resistance Among Invasive *Streptococcus penumoniae* Isolates, JAMA, Oct. 17, 2001; 286 (15):1857-62. (Abstract).
Iba et al., Comparison Between Continuous intravenous and Oral Administration of 5-FU with LV, Gan To Kagaku Ryoho. Apr. 1999; 26(5):631-5. (Abstract).
Jacobs, Pharmacodynamic Approach to Antimicrobial Treatment for Respiratory Infections, Department of Pathology, Case Western Reserve University, 2006.
Kaplan et al., Macrolide Therapy of Group A Streptococcal Pharyngitis: 10 Days of Macrolide Therapy (Clarithromycin) is More Effective in Streptococcal Eradication Than 5 Days (Azithromycin), Clin Infect Dis. Jun. 15, 2001; 32 (12):1798-802. Epub May 21, 2001. (Abstract).
Klugman, Bacteriological Evidence of Antibiotic Failure in Pneumococcal Lower Respiratory Tract Infections, Eur Respir J 2002; 20 Suppl. 36, 3s-8s.
Kramer et al., Statistical Optimisation of Diclofenac Sustained Release Pellets Coated with Polymethacrylic Films, Int J Pharm. Apr. 30, 2003; 256(1-2):443-52. (Abstract).
Laine et al., Frequency and Clinical Outcome of Potentially Harmful Drug Metabolic Inteactions in Patients Hospitalized on Internal and Pulmonary Medicine Wards: Focus on Warfarin and Cisapride, Therapeutic Drug Monitoring. 22 (5):503-509, Oct. 2000. (Abstract).
Laine et al., Frequency and Clinical Outcome of Potentially Harmful Drug Metabolic Interactions in Patients Hospitalized on Internal and Pulmonary Medicine Wards: Focus on Warfarin and Cisapride, Therapeutic Drug Monitoring. 22(5):503-509, 2000.
Lamb et al., Ceftriaxone: An Update of its Use in the Management of Community-Acquired and Noscocomial infections, Drugs, 2002:62(7)1041-89. (Abstract).
Lerner-Tung et al., Pharmacokinetics of Intrapericardial Administration of 5-Fluorouracil, Cancer Chemother Pharmacol. 1997; 40(4):318-20. (Abstract).
Lin et al., Multiple-Dose Pharmacokinetics of Ceftibuten in Healthy Volunteers, Antimicrobial Agents and Chemotherapy, Feb. 1995, p. 356-358.

(56) References Cited

OTHER PUBLICATIONS

Lindsey et al., Extraction of Antibiotics From Agricultural Wastewater, USGS, 220th ACS Meeting Washington, D.C.; Aug. 20-24, 2000, (Abstract).
Livermore et al., Activity of Ertapenem Against *Neisseria gonorrhoeae*, Journal of Antimicrobial Chemotherapy 2004 54(1):280-281.
Lovmar et al., Kinetics of Macrolide Action, The Josamycin and Erythromycin Cases, J. Biol. Chem., vol. 279, Issue 51, 53506-53515, Dec. 17, 2004.
Mainz et al., Pharmacokinetics of Lansoprazole, Amoxicillin and Clarithromycin After Simultaneous and Single Administration, Journal of Antimicrobial Chemotherapy (2002) 50, 699-706.
Marten et al., Monthly Report, Jul. 2004, Pulsatile Dosing of Antifungal Compounds, UMBC; to Dr. Robert J. Guttendorf, Advancis Pharmaceutical Corp.
Mazzei et al., How Macrolide Pharmacodynamics Affect Bacterial Killing, Infect Med 16(sE):22-28, 1999, (Abstract).
Nightingale, Pharmacokinectics and Pharmacodynamics of Newer Macrolides, Pediatric Infectious Disease Journal. 16(4):438-443, Apr. 1997. (Abstract).
Olofinlade et al. Anal Carcinoma: A 15-Year Restrospective Analysis , Scand J Gastroenterol 2000:35; 1194-1199.
Pacifico et al., Comparative Efficacy and Safety of 3-Day Azithromycin and 10-Day Penicillin V Treatment of Group A Beta-Hemolytic Streptcoccal Pharyngitis in Children, Antimicrobiol Agents and Chemotherapy, Apr. 1996, 1005-1008, vol. 40, No. 4. (Abstract).
Parmar-Lapasia et al., A Comparison of Two Macrolide Antibiotics in the Treatment of Community-Acquired Infections, P & T (Pharmacy & Therapeutics), Oct. 2003, vol. 28, No. 10.
Peters et al., Fluorouracil (5FU) Pharmacokinetics in 5FU Prodrug Formulations with a Dihydropyrimidine Dehydrogenase Inhibitor, Journal of Clinical Oncology, vol. 19, Issue 22 Nov. 15, 2001: 4267-4269.
Polak, Pharmacokinetics of Amphotericin B and Flucytosine, Postgrad Med J. Sep. 1979; 55(647):667-70. (Abstract).
Porter et al., Antibiotics and Infectious Diseases in Otolaryngology—HNS, Grant Rounds Presentation, UTMB, Dept. of Otolaryngology, May 8, 2002.
Ramminger et al., Transition-Metal Catalyzed Synthesis of Ketoprofen, J. Braz, Chem. Soc. vol. 11, No. 2, 105-111, 2000.
Ramu, Compounds and Methods that Reduce the Risk of Extravasation Injury Associated with the Use of Vesicant Antineoplastic Agents, Baylor College of Medicine, Aug. 6, 1998.
Ranga Rao et al., Influence of Molecular Size and Water Solubility of the Solute on its Release from Swelling and Erosion Controlled Polymeric Matrices, Journal of Controlled Release, 12 (1990) 133-141.
Reza et al., Comparative Evaluation of Plastic, Hydrophobic and Hydrophilic Polymers as Matrices for Controlled-Release Drug Delivery, J. Pharm. Pharmaceut. Sci., 6(2):282-291, 2003.
Richardson, The Discovery and Profile of Fluconazole, J Chemother. Feb. 1990;2(1):51-4 (Abstract) and Houang et al., Fluconazole Levels in Plasma and Vaginal Secretions of Patients After a 150-Milligram Single Oral Dose and Rate of Eradication of Infection in Vaginal Candidiasis, Antimicrob Agents Chemother. May 1990; 34(5):909-10. (Abstract).
Rivkees et al., Dexamethasone Treatment of Virilizing Congenital Adrenal Hyperplasia: The Ability to Achieve Normal Growth, Pediatrics 2000; 106; 767-773.
Roblin et al., In Vitro Activity of a New Ketolide Antibiotic; HMR 3647, Against *Chlamydia pneumoniae*, Antimicrob Agents Chemother. Jun. 1998; 42(6): 1515-15116.
Santini et al., The Potential of Amifostine: From Cytoprotectant to Therapeutic Agent, Haematologica Nov. 1999; 84(ii): 1035-1042.
Sanz et a., Cefepime Plus Arnikacin Versus Piperacillin-Tazobactam Plus Amikacin for Initial Antibiotic Therapy in Hematology Patients with Febrile Neutropenia: Results of an Open, Randomized, Multicentre Trial, Journal of Antimicrobial Chemotherapy (2002) 50, 79-88.
Schaad et al., Azithromycin Versus Penicillin V for Treatment of Acute Group A Streptococcal Pharyngitis, The Pediatric Infectious Disease Journal: vol. 21(4) Apr. 2002, pp. 304-308.
Schweizer et al., "Single Shot" Prevention in Abdominal Surgery. Antibiotics with Long Half-Life (Cefriazone, Omidazole) vs. Antibiotics with Short Half-Life (Cefazolin, Metronidazole, Clindamycin), Helv Chir Acta. Apr. 1994; 60 (4):483-8. (Abstract).
Shvartzman et al., Treatment of *Streptococcal pharyngitis* with Amoxycillin Once a Day, BMJ vol. 306, pp. 1170-1172, May 1, 1993.
Stringer et al., Section 3: Diseases of the Ear, Part 4: Inner Ear, Chapter 46: Ototoxicity, Paparella: vol. II, Otology and Neuro-Otology, W B. Saunders Co., 3rd Edition, 1990.
Suda et al., The Synthesis and In Vitro and In Vivo Stability of 5-Fluorouracil Prodrugs Which Possess Serum Albumin binding Potency, Biol Pharm Bull. Sep. 1993;16(9):876-7. (Abstract).
Sandip et al., Controlled Release Formulation of Tramadol Hydrochloride Using Hydrophillic and Hydrophobic Matrix System, AAPS PharmSciTech 2003; 4(3) Article 31.
Todar's Online Textbook of Bacteriology, Antimicrobial Agents Used in Treatment of Infectious Disease 2002 Kenneth Todar University of Wisconsin-Madison Department of Bacteriology.
Vanderkooi et al., Antimicrobial Resistance and the Pneumococcus, Infectious Diseases and Microbiology. vol. 3, Issue 5, May 2004.
Villalobos et al., Pharmacokinetics and Pharmacodynamics of Antibacterial Agents in Pediatrics: A Practical Approach, Jacksonville Medicine, Aug. 1998.
Waters, Colorectal Cancer-Drug Treatment, Hospital Pharmacist, vol. 11, pp. 17-192, May 2004.
Wattenberg, Prevention of Carcinogenesis of the Respiratory Tract by Chemopreventive Agents Delivered by Aerosol, International Society of Cancer Chemoprevention, vol. 1, No. 5, Jan. 2003.
Whitehead et al., Amoxycillin Release From a Floating Dosage Form Based on Alginates, International Journal of Pharmaceutics 210 (2000) 45-49.
Yousef et al., Combined Action of Amoxycillin and Dicloxacillin Against *Staphylococcus aureus* In Vitro, Pharmazie Sep. 1985; 40(9):650-1, (Abstract).
About Macrolides, About That Bug.com (2006).
Amoxycillin (As Trihydrate), Moxyvit (2003).
Amoxicillin + Clavulanate, PetPlace.com (2005).
Answers.com, Macrolide (2006).
Antimetabolites, GPnotebook (2005).
Augmentin, Product Information, GiaxoSmithKline, Physicians Desk References, Jun. 2004, pp. 1421-1433.
Augmentin XR (PDR entry for) (GlaxoSmithKline), (Amoxicillin/ Clavulanate Potassium), Extended Release Tablets, Jun. 2004.
Beta Lactam Antibiotics, Health 24.com (2005).
Biaxin XL, Once-Daily Biaxin XL Clarithromycin Extended-Release Tablets, Abbott Laboratories Online (2004).
Biaxin XL, Once-daily, Clarithromycin Extended-Release Tablets (2005).
Biaxin Filmtab, Biaxin XL Filmtab, Biaxin Granules, pp. 1-25, Abbott Laboratories (2005).
Body Chemistry, Acid Alkaline Foods, Acid Reflux? Gas, Acid Indigestion, Acid/Alkaline Balance, Printed from timberware.com/ chemistry.html on Jan. 2, 2012.
Citizen Petition, McNeil Consumer & Specialty Pharmaceuticals, Mar. 19, 2004.
Clarithromycin Extended-Release Scientific Posters Presented to the 39th Interscience Conference on Antimicrobial Agents and Chemotherapy (ICAAC). San Francisco, Sep. 26-29, 1999.
Clearance and the Elimination Rate Constant, Ke (Elimination Rate)—Half-Life, Oct. 14, 2002.
Complementary Medicine Saves Money, Medicine, Greenhealthwatch.com, Collection of medical headlines citing to sources dated between May 1, 1997 and Aug. 10, 2002.
Declaration of Michael J. Rybak from the prosecution history of U.S. Appl. No. 09/792,092; Sep. 23, 2002.

(56) References Cited

OTHER PUBLICATIONS

Dispensing Errors With Depakote, New Formulation Creates Confusion, Patient Safety, Practitioners Reporting News, USP Issued Mar. 3, 2001.
Drugs.com, Drug Information for Diclofenac (Topical) (2006).
Drug, Bio-Affecting and Body Treating Compositions (Class 424). 475 Sustained or differential release, United States Patent and Trademark Office, Classification Definitions as of Jun. 30, 2000.
Emulsions, Secundum Artem, vol. 4, No. 1, printed from www.padocklabs.com/html/resource/pdf/sed Artem 4.1.pdf on Jan. 2, 2012.
Encyclopedia Britannica Online, Types of Drugs>Antimicrobial Drugs>Antibiotics>Macrolides, Mar. 28, 2006.
Excenel, Swine Health Management, Prewean Program. Pfizer Salud Animal (2005).
Fabrication of Metronidazole Strips, 996 Die Pharmazie 50(1995) February, No. 2.
Five vs. 10 Days of Therapy for Streptococcal Pharyngitis, American Family Physician, Feb. 15, 2001.
Food and Drug Administration Center for Drug Evaluation and Research Approved Drug Products With Therapeutic Equivalence Evaluations, 24th Edition, Feb. 26, 2004.
Getting a Drug into the Body: Absorption, from How Drugs Work: Basic Pharmacology for Healthcare Professionals, Hugh McGarock, 2nd Edition, May 2005.
Highlights on Antineoplastic Drugs, Pharmacia, vol. 11, No. 4, 1993.
Jock Itch and Other dermatophytes. Mycolog.com (Sep. 2002).
Klarithran, Ranbaxy(SA)(PTY) LTD, Jun. 2005.
Klucel Hydroxypropylcellulose (HPC). Hercules Incorporated (2004).
MedicineNet.com, Generic Name: Acyclovir, Brand Name: Zovirax, Dec. 31, 1997.
Meeting the Challenge of a New Generation of Respiratory Pathogens, MAC (2001).
The Merck Index, An Encyclopedia of Chemicals, Drugs, and Biologicals, Twelfth Edition, pp. 397-398 (1996).
Methods of Formulation Controlled Release Products Outside of the Claims of Forest Laboratory Patents U.S. 4,369,172 and U.S. 4,389,393, Technical Information Dow Chemical Feb. 1991.
Miconazole, The Merck Index Results-Form view, Monograph No. 06202 (2005).
Mode of Action of Macrolides in Blocking Translation During Bacterial Protein Synthesis: Blocking Peptidyltransferase, Doc Kaiser's Microbiology Home Page, Oct. 13, 2004.
Module 8—Therapeutics. May 25, 2002, Newcastle. BPAIIG Immunology/Infectious Diseases Training Programme, Module: Therapeutics.
*Neisseria meningitidis*, The Doctor's Doctor, Nov. 8, 2004.
New-Generation Aromatase Inhibitor for Breast Cancer: Anastrozole Challenges Tamoxifen in First-Line Therapy, 10th European Cancer Conference (ECCO 10), Vienna, Austria/Sep. 12-16, 1999.
New Product Newswire, Drug Topics Archive, Aug. 5, 2002.
Nitrofurantoin, Eckerd Prescription Advisory, Feb. 15, 2001.
Nursing, Cancer Nursing: Principles and Practice, Fifth Edition, Jones and Barlett Publishers, 2000.
Oral Capecitabine Should Improve Convenience of Chemoradiation for Locally Advanced Rectal Cancer—New Treatment Appears to be Safe and Effective, PeerView Press, Chemotherapy (ICAAC), Sep. 27-30, 2002; San Diego, CA, 40th Annual Meeting of Infectious Diseases Society.
Oral Extended (Controlled) Release Dosage Forms, In Vivo Bioequivalence and In Vitro Dissolution Testing, Office of Generic Drugs (1993).
Pharmaceuticals, Pharmacos Unit F2 Pharmaceuticals V 6.0, Eudralex Collection 3AQ19a 1992.
Physicians Desk Reference, PDR 57 Edition 2003, p. 402/Abbott.
Principles of Diagnosis of Infectious Diseases and Antimicrobial Therapy, Antibiotic Guideline, Dr. Norman Miller et al., 2nd Edition, Chapters 1-3, printed from www.sassit.co.za/Journal/Infections/Antibiotics/Middes/AntibioticGuide/pdf printed on Jan. 2, 2012.
Procardia XL (Nifedipine) Extended Release Tablets for Oral Use, 69-4467-00-8, Pfizer Labs, Aug. 2003.
Summary of Product Characteristics, Doxycycline Capsules BP 50mg, Nov. 2001.
Sustained or Differential Release Type, USPTO Classification Definitions (Dec. 2002 Edition) 964.
Sustained-Release Dosage Forms, Degussa, Rohm Pharma Polymers, printed from www.solimide, eu/en/pharmapolymers/service/literature/practical_course.Par.0001.TROW.0010.Tcell.0003.File, tmp/pc_30_sustained.pdf on Jan. 2, 2012.
Testicular Cancer: Questions and Answers, Cancer Facts, National Cancer Institute, Aug. 14, 2003.
Traditional Chemotherapy, Chapter 25 from Prevention and Therapy of Cancer and Other Common Disease: Alternative and Traditional Approaches; Infomedix 1996.
Grange et al. Pharmacokinetics of amoxycillin/clavulanic acid in serum and ascitic fluid in cirrhotic patients. Apr. 12, 1989. Abstract only.
Craig, "Pharmacokinetic/Pharmacodynamic Parameters: Rationale for Antibacterial Dosing of Mice and Men", Clinical Infectious Diseases, Jan. 1998, vol. 26, pp. 1-12, entire document, especially Fig. 5 and 6.
Kaye et al. The Clinical Pharmacokinetics of a New Pharmacokinetically Enhanced Formulation of Amoxicillin/Clavulanate, Clinical Therapeutics, 2001, 23(4), 578-584.
Barry et al. In Vitro Activities of 12 Orally Administered Agents against Four Species of Bacterial Respiratory Pathonges from U.S. Medical Centers in 1992 and 1993, Antimicrobial Agents and Chemotherapy, 1994, 38(10), 2419-2425.

\* cited by examiner

MODIFIED RELEASE AMOXICILLIN PRODUCTS

This invention is directed to amoxicillin products, and to methods of use thereof.

In the treatment of bacterial infections amoxicillin is often dosed in immediate release (IR) formulations that may require multiple administrations over the course of any given 24-hour period. As is known in the art, such dosing regimens may be twice-a-day (b.i.d.), whereby the composition is administered every 12 hours; three times daily (t.i.d.), whereby the composition is administered every 8 hours; four times daily (q.i.d.), whereby the composition is administered every 6 hours; or such dosing regimens may even conceive of dosing the composition in excess of four administrations per day.

Amoxicillin is also available in a modified release formulation, e.g., as sold under the trademark AUGMENTIN XR.

The present invention is directed to an amoxicillin product and use thereof in which all or a portion of the amoxicillin is present as a modified release component.

In one embodiment, the amoxicillin product is formulated in a manner such that (x) the amoxicillin product has a mean AUC such that the ratio of (i) the portion of the mean AUC for the amoxicillin of the product during the period from 2 hours after administration to 5 hours after administration to (ii) the portion of the mean AUC of the amoxicillin of the product during the period extending from administration to 2 hours after administration is at least 2.0:1 and (y) the ratio of (iii) the portion of the mean AUC for the amoxicillin of the product during the period extending from 5 hours after administration to 12 hours after administration to (ii) the portion of the mean AUC of the amoxicillin of the product during the period extending from administration to 2 hours after administration is at least 1.1:1.

An AUC (area under the curve) for a specified period is referred to as a "partial AUC" for the period.

As used in the Specification and Claims $AUC_{(0-2)}$ means the portion of the amoxicillin AUC that is determined substantially in accordance with the procedure of Example 1 from time 0 to 2 hours after the administration of the amoxicillin product.

$AUC_{(2-5)}$ means the portion of the amoxicillin AUC that is determined substantially in accordance with the procedure of Example 1 from time 2 to 5 hours after the administration of the amoxicillin product.

$AUC_{(5-12)}$ means the portion of the amoxicillin AUC that is determined substantially in accordance with the procedure of Example 1 from time 5 to 12 hours after the administration of the amoxicillin product.

In one embodiment, the amoxicillin product has an $AUC_{(2-5)}$ to $AUC_{(0-2)}$ ratio that is at least 2.2:1 and in another at least 2.4:1.

In another embodiment, the $AUC_{(5-12)}$ to $AUC_{(0-2)}$ ratio is at least 1.2:1 or at least 1.3:1.

In general, the $AUC_{(2-5)}$ to $AUC_{(0-2)}$ ratio does not exceed 10:1, or in some cases 8:1 or in other cases 6:1.

In general, the $AUC_{(5-12)}$ to $AUC_{(0-2)}$ ratio does not exceed 10:1, or in some cases 8:1 or in other cases 6:1.

For the purposes of the specification and claims, an amoxicillin product may be tested substantially in accordance with Example 1 by use of either the high fat or low fat Fed State Regimen of Example 1, and such amoxicillin product is deemed to fall within a specified range of partial AUC ratios if it falls within such range by testing substantially in accordance with either one of such Fed State Regimens.

As used herein the term "amoxicillin" shall be broadly interpreted to include not only that active ingredient, but also all, polymorphs, salts, and/or hydrates thereof.

As known in the art an AUC (area under the curve) for amoxicillin in human plasma is a pharmacokinetic profile of the amoxicillin of the product in human plasma after administration of the amoxicillin product to a human, where AUC is the area under the curve resulting from a plot of the amoxicillin concentration in human plasma as a function of time after administration such that the Y axis is the concentration of amoxicillin in human plasma after administration of the amoxicillin product and the X axis is time after administration.

The hereinabove ratios are determined substantially in accordance with the procedure set forth in Example 1 wherein the pharmacokinetic profile is determined from administration of a single dose of amoxicillin product in the fed state substantially in accordance with Example 1, human plasma samples are obtained and analyzed substantially in accordance with Example 1 and the AUC ratios are determined substantially in accordance with Example 1.

Example 1 is provided as an analytical tool for determining whether or not an amoxicillin product has the hereinabove described partial AUC ratios. Such analytical tool of the Example does not limit the invention to administering to a human the amoxicillin product only in the fed state; and does not limit the invention to treating a patient in accordance with the protocol of Example 1.

As a result, as used in the Specification and Claims a partial AUC ratio is one determined in the fed state substantially in accordance with Example 1, even though the amoxicillin product is used or administered in a manner different from Example 1, and even if in any regulatory filing for an amoxicillin product, the AUC and/or partial AUC is determined in a manner different from Example 1.

In an embodiment of the invention, there is provided an amoxicillin product that includes at least one modified release component wherein such product when administered in the fasted state has an equivalent extent of absorption to that of such product when administered in the fed state.

As used herein an "equivalent extent of absorption" means that the absorption in the fasted state is within 80% to 125% of the absorption in the fed state with a 90% confidence interval, as set forth in FDA Guidance for Industry—Food-Effect Bioavailability and Fed Bioequivalence Studies, December 2002.

In accordance with such guidelines, a protocol for determining extent of absorption in the "fasted state" means that following an overnight fast of at least 10 hours, subjects should be administered the drug product with 240 mL (8 fluid ounces) of water. No food should be allowed for at least 4 hours post-dose. Water can be allowed as desired except for one hour before and after drug administration. Subjects should receive standardized meals scheduled at the same time in each period of the study. In accordance with such guidelines a protocol for determining extent of absorption in the "fed state" means that following an overnight fast of at least 10 hours, subjects should start the recommended meal 30 minutes prior to administration of the drug product. Study subjects should eat this meal in 30 minutes or less; however, the drug product should be administered 30 minutes after start of the meal. The drug product should be administered with 240 mL (8 fluid ounces) of water. No food should be allowed for at least 4 hours post-dose. Water can be allowed as desired except for one hour before and after drug administration. Subjects should receive standardized meals scheduled at the same time in each period of the study.

The "Recommended Meal" means: A high-fat (approximately 50 percent of total caloric content of the meal) and high-calorie (approximately 800 to 1000 calories) meal is recommended as a test meal for food-effect BA (bioavailability) and fed BE (bioequivalence) studies. This test meal should derive approximately 150, 250, and 500-600 calories from protein, carbohydrate, and fat, respectively. The procedure of Example 1 complies with such guidelines for fasted and fed states.

Extent of absorption is generally determined by area under the curve (AUC). Two types of AUC are typically reported and are typically referred to as $AUC_{0-t}$, where the AUC is calculated over the range from time zero until the last plasma sample was taken, time t, and $AUC_{0-inf}$ often denoted $AUC_{inf}$ where the $AUC_{t-inf}$ is calculated and added to $AUC_{0-t}$. $AUC_{t-inf}$ is extrapolated from time t until the infinity point, which is the time point where the active ingredient concentration reaches 0 determined by extrapolation from the last measured concentration based on the elimination rate determined from the individual subject data.

An amoxicillin product that includes at least a modified release component that is formulated to have the partial AUC ratios as hereinabove described may be produced in a wide variety of forms and dosages of amoxicillin and may be administered in accordance with a variety of different protocols; for example, once-a-day, twice-a-day, three times a day.

In one embodiment, the product includes an immediate release component and a delayed release component.

In another embodiment, the product includes an immediate release component and two or more delayed release components.

In another embodiment, the product includes one, two or three or more delayed release components and is free of an immediate release component.

In another embodiment, the product includes one, two or more extended (sustained) release components and is free of an immediate release component.

In a further embodiment, the product includes an immediate release component and one, two or more extended release components.

In yet another embodiment, the product includes an immediate release component and a combination of one or more delayed release components and one or more extended release components.

As used herein and as known in the art, an immediate release component is one in which the initiation of release, and/or the rate of release, of active ingredient is not substantially delayed, and/or slowed, and/or sustained, after administration of the product. As used herein and as known in the art, a modified release component is other than an immediate release component. Non-limiting examples of such modified release components include: delayed release component(s) which is one where after the delay the release is not sustained over a period of time, and a sustained (or extended) release component, which is one where release of active ingredient is sustained over a period of time and/or combinations of the foregoing. Immediate release, delayed released and sustained (extended) release components are components and terminology well known in the art and the formulation thereof is well within the skill of the art. The use of various combinations of the aforementioned components will be apparent to those of ordinary skill in the art in view of the disclosures herein, further guided by the disclosures of U.S. patent application Ser. Nos. 10/894,787; 10/894,786; 10/894,994; 10/917,059; 10/922,412; and 10/940,265; and by the disclosures of U.S. Pat. Nos. 6,544,555; 6,623,757; and 6,669,948; all of which are hereby incorporated by this reference in their entireties. In accordance with an embodiment of the invention, irrespective of the various components used in the amoxicillin product that includes at least one modified release, such components are formulated such that the amoxicillin product has the partial AUC ratios hereinabove described.

In accordance with one embodiment of the invention, there are at least two components (at least one of which is a modified release component). One of the at least two components is an immediate release component, whereby initiation of release of the amoxicillin therefrom is not substantially delayed after administration of the amoxicillin composition, or is a delayed release component, whereby initiation of release of the amoxicillin therefrom is substantially delayed after administration of the amoxicillin composition. The second of the at least two components is a delayed release component (each delayed release component may be a pH sensitive or a non-pH sensitive delayed release component, depending on the type of amoxicillin composition), whereby the amoxicillin released therefrom is delayed until after initiation of release of the amoxicillin from the immediate release or first delayed release component. More particularly, the amoxicillin released from the second of the at least two components achieves a $C_{max}$ (maximum concentration in the plasma) at a time after the amoxicillin released from the first of the at least two components achieves a $C_{max}$ in the plasma.

In accordance with one embodiment of the invention, there are at least three components (at least one of which is a modified release component). One of the at least three components is an immediate release component whereby initiation of release of the amoxicillin therefrom is not substantially delayed after administration of the amoxicillin composition. The second and third of the at least three components are delayed release components (each of which may be a pH sensitive or a non-pH sensitive delayed release component, depending on the type of amoxicillin composition), whereby the amoxicillin released therefrom is delayed until after initiation of release of the amoxicillin from the immediate release component. More particularly, the amoxicillin released from the second of the at least three components achieves a $C_{max}$ (maximum concentration in the plasma) at a time after the amoxicillin released from the first of the at least three components achieves a $C_{max}$ in the plasma, and the amoxicillin released from the third component achieves a $C_{max}$ in the plasma after the $C_{max}$ of amoxicillin released from the second component.

In one embodiment, the second of the at least three components initiates release of the amoxicillin contained therein at least one hour after the first component, with the initiation of the release therefrom generally occurring no more than six hours after initiation of release of amoxicillin from the first component of the at least three components.

As hereinabove indicated, some embodiments of the amoxicillin composition may contain two, three, four, or more different components (provided that at least one is a modified release component).

In one three-component embodiment, the amoxicillin released from the third component reaches a $C_{max}$ at a time later than the $C_{max}$ is achieved for the amoxicillin released from each of the first and second components. In a preferred embodiment, release of amoxicillin from the third component is started after initiation of release of amoxicillin from both the first component and the second component. In one embodiment, $C_{max}$ for amoxicillin released from the third component is achieved within eight hours.

In another three-component embodiment the release of amoxicillin from the second component may be contemporaneous with initiation of release of amoxicillin from the first component.

In another three-component embodiment the release of amoxicillin from the third component may be contemporaneous with initiation of release of amoxicillin from the second component.

In another embodiment, the amoxicillin composition may contain four components (at least one of which is a modified release component), with each of the four components having different release profiles, whereby the amoxicillin released from each of the four different components achieves a $C_{max}$ at a different time.

In one preferred embodiment, the amoxicillin product contains at least two or at least three or at least four different components each with a different release profile, $C_{max}$ for all the amoxicillin released from the amoxicillin product in those is achieved in less than twelve hours, and more generally is achieved in less than eleven hours.

In one embodiment, the amoxicillin product is a once-a-day composition, whereby after administration of the amoxicillin product, no further composition is administered during the day; i.e., the regimen is that the product is administered only once over a twenty-four hour period. Thus, in accordance with this embodiment, there is a single administration of an amoxicillin product with the amoxicillin being released in a manner such that overall amoxicillin release is effected with different release profiles in a manner such that the overall $C_{max}$ for the amoxicillin composition is reached in less than twelve hours. The term single administration means that the total amoxicillin administered over a twenty-four hour period is administered at the same time, which can be a single dosage unit (tablet, capsule or sprinkle/sachet) or two or more thereof, provided that they are administered at essentially the same time.

In one embodiment, such once-a-day product is comprised of an immediate release component and two delayed release components wherein the first delayed release component initiates release of amoxicillin after release of amoxicillin from the immediate release component and the second delayed release component initiates release of amoxicillin after release of amoxicillin from the first delayed release component.

In a once-a-day amoxicillin product, such product has partial AUC ratios as hereinabove described.

In one embodiment, the amoxicillin product is a twice-a-day product, whereby after an initial administration of the amoxicillin product, there is a further administration of the amoxicillin product at another time during the day; i.e., the regimen is that the composition is administered only twice over a twenty-four hour period.

In one embodiment, the twice-a-day amoxicillin product includes two or more components with one of such two components being an immediate release component and the other of the two components being a modified release component.

In another embodiment the twice-a-day amoxicillin product contains one immediate release component and two or more modified release components, with a particular embodiment including two modified release components.

In a twice-a-day amoxicillin product, such product has partial AUC ratios as hereinabove described.

Thus, in accordance with one embodiment, there is a b.i.d. administration of an amoxicillin product with the amoxicillin being released in a manner such that overall amoxicillin release is effected with different release profiles in a manner such that the overall $C_{max}$ for each of the two administrations of the product is reached in less than twelve hours after each administration. The dose administered at each of the two administrations can be a single amoxicillin product or a plurality of amoxicillin products.

In one embodiment, the hereinabove described amoxicillin products having the hereinabove described partial AUC ratios have an extent of absorption ($AUC_{o\text{-}inf}$) that is at least 75% and in a preferred embodiment at least 80% of the extent of absorption ($AUC_{o\text{-}inf}$) of an amoxicillin product that provides for only immediate release of amoxicillin. In general, the extent of absorption ($AUC_{o\text{-}inf}$) of an amoxicillin product of the invention does not exceed the extent of absorption ($AUC_{o\text{-}inf}$) of an amoxicillin product that provides for only immediate release of amoxicillin. In comparing the products to determine extent of absorption, the $AUC_{o\text{-}inf}$ is determined in either the fed state or the fasted state in accordance with the hereinabove referred to FDA Guidance for Industry and each of the products has the same amount of amoxicillin.

When administering the amoxicillin product orally to a human, such product may be taken in the fed state or fasted state, preferably in the fed state.

As known in the art, oral administration of such a product to a human in a fed or fasted state has a meaning different from the FDA requirements for testing extent of absorption. In terms of administering a product to a human for use of a product, fed state means in conjunction with food (immediately prior to, with or immediately after intake of food). The fasted or non-fed state means other than in conjunction with the intake of food.

It is to be understood that when it is disclosed herein that a component initiates release after another component, such terminology means that the component is designed and is intended to produce such later initiated release. It is known in the art, however, notwithstanding such design and intent, that some "leakage" of antibiotic may occur. Such "leakage" is not "release" as used herein.

The amoxicillin product of the present invention, as hereinabove described, may be formulated for administration by a variety of routes of administration. For example, the amoxicillin composition may be formulated in a way that is suitable for topical administration; administration in the eye or the ear; rectal or vaginal administration; as a nasal preparation; by inhalation; as an injectable; or for oral administration. In a preferred embodiment, the amoxicillin composition is formulated in a manner such that it is suitable for oral administration.

For example, in formulating the amoxicillin product for topical administration, such as by application to the skin, the components, each of which contains amoxicillin, may be formulated for topical administration by including such components in an oil-in-water emulsion, or a water-in-oil emulsion. In such a formulation, an immediate release component may be in the continuous phase, and a delayed release component may be in a discontinuous phase. The formulation may also be produced in a manner for delivery of three components as hereinabove described. For example, there may be provided an oil-in-water-in-oil emulsion, with oil being a continuous phase that contains the immediate release component, water dispersed in the oil containing a first delayed release component, and oil dispersed in the water containing a third delayed release component.

It is also within the scope of the invention to provide an amoxicillin product in the form of a patch, which includes amoxicillin components having different release profiles, as hereinabove described.

In addition, the amoxicillin product may be formulated for use in the eye or ear or nose, for example, as a liquid emulsion.

For example, the component may be coated with a hydrophobic polymer whereby a component is in the oil phase of the emulsion, and a component may be coated with hydrophilic polymer, whereby a component is in the water phase of the emulsion.

Furthermore, the amoxicillin product having at least one modified release component (whether or not combined with additional components to provide a plurality of different release profiles) may be formulated for rectal or vaginal administration, as known in the art. This may take the form of a cream, an emulsion, a suppository, or other dissolvable component similar to those used for topical administration.

The amoxicillin product may include an amount of amoxicillin from about 200 mg to about 2500 mg, depending on the form of the product. As non-limiting examples, the amoxicillin product may contain 475 mg or 775 mg or 1250 mg or 1550 mg or 2325 mg of amoxicillin.

In a preferred embodiment, the amoxicillin product is formulated in a manner suitable for oral administration. Thus, for example, for oral administration, each of the components may be used as a pellet or a particle, with a pellet or particle then being formed into a unitary pharmaceutical composition, for example, in a capsule, or embedded in a tablet, as a sprinkle, or suspended in a liquid for oral administration. In one non-limiting embodiment, the tablet may be a rapidly disintegrating tablet, whereby the various components of the product are released upon ingestion for further transport into the intestine in the form of pellets or granules.

Alternatively, in formulating an oral delivery system, each of the components of the composition may be formulated as a tablet, with each of the tablets being put into a capsule to produce a unitary amoxicillin product. Thus, as a non-limiting example, a three component amoxicillin product may include a first component in the form of a tablet that is an immediate release tablet, and may also include two or more additional tablets, each of which provides for a delayed release or a sustained release of the amoxicillin, as hereinabove described.

The amoxicillin product may be in the form of a sprinkle product; for example by placing the various components of the product in particulate form (for example as pellets) in a sachet, capsule or other form that can be used for administering the components in particulate form at the same time.

The formulation of an amoxicillin product including at least three components with different release profiles for different routes of administration is deemed to be within the skill of the art from the teachings herein. As known in the art, with respect to delayed release, the time of release can be controlled by a variety of mechanisms such as pH trigger point, coating thickness, choice of polymer, choice of plasticizer, osmotic pressure, physical swelling pressure and combinations of the foregoing.

In formulating an amoxicillin product in accordance with one embodiment of the invention, an immediate release component generally comprises about 45% of the total amoxicillin dose in the product, a first delayed release component generally comprises about 30% of the total amoxicillin dose in the product, and a second delayed release component generally comprises about 25% of the total amoxicillin dose in the product (all by weight). This embodiment is non-limiting, and when the disclosures herein are considered along with the entirety of the further knowledge that necessarily informs the level of ordinary skill in the art, the person of ordinary skill in the art will readily appreciate component percentages differing from those noted in the non-limiting embodiment, which percentages when combined to form an amoxicillin product has the hereinabove described partial AUC ratios.

In accordance with an embodiment of the present invention, each of the components contains amoxicillin; however, each of the components may contain another antibiotic or other type of active ingredient.

In the embodiments hereinabove described, the amoxicillin product has the partial AUC ratios as hereinabove described.

The Immediate Release Component

The immediate release portion of this system can be a mixture of ingredients that breaks down quickly after administration to release the amoxicillin. This can take the form of either a discrete tablet, pellet or granule that is mixed in with, or compressed with, the other components in the product.

In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, sorbitan monooleate, polyoxyethylene sorbitan monooleate, glyceryl monostearate, glyceryl monooleate, glyceryl monobutyrate, one of the non-ionic surfactants such as the Pluronic line of surfactants, or any other material with surface active properties, or any combination of the above.

The Non-pH Sensitive Delayed Release Component

The components in this composition are the same as the immediate release unit, but with additional polymers integrated into the composition, or as coatings over the pellet or granule.

Several methods to affect a delayed release with non-pH dependent polymers are known to those skilled in the art. These include soluble or erodible barrier systems, enzymatically degraded barrier systems, rupturable coating systems, and plugged capsule systems among others. These systems have been thoroughly described in the literature (see "A Review of Pulsatile Drug Delivery" by Bussemer and Bodmeier in the Winter 2001 issue of American Pharmaceutical Review) and formulations and methods for their manufacture are hereby incorporated by reference.

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit), propylene glycol, and ethylcellulose.

Typically these materials can be present in the range of 0.5-40% (W/W) of this component.

The pH Sensitive (Enteric) Release Component

The components in this composition are the same as the immediate release component, but with additional polymers integrated into the composition, or as coatings over the pellet or granule to delay release.

The kind of materials useful for this purpose can be, but are not limited to, cellulose acetate pthalate, Eudragit L, Eudragit S, Eudragit FS, and other pthalate salts of cellulose derivatives.

These materials can be present in concentrations from 4-30% (W/W).

Sustained Release Component

The components in this composition are the same as the immediate release component, but with additional polymers integrated into the composition, or as coatings over a tablet, pellet or granule to provide a sustained release of the pharmaceutical.

The kind of materials useful for this purpose can be, but are not limited to, ethylcellulose; hydroxypropylmethylcellulose; hydroxypropylcellulose; hydroxyethylcellulose; carboxymethylcellulose; methylcellulose; nitrocellulose;

Eudragit R; Eudragit RS; and Eudragit RL; Carbopol; or polyethylene glycols with molecular weights in excess of 8,000 daltons.

These materials can be present in concentrations from 4-40% (W/W).

When it is desired to delay initiation of release of the sustained release component, an appropriate coating may be used to delay initiation of the sustained release, such as a pH sensitive or a non-pH sensitive coating.

The Non-pH Sensitive Coating for Sustained Release Component

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit RS), cellulose acetate, and ethylcellulose.

Typically these materials can be present in the range of 0.5-25% (W/W) of this component. Preferably the materials are present in an amount just enough to provide the desired in vivo lag time and $T_{max}$.

The pH Sensitive Coating for Sustained Release Component

The kind of materials useful for this purpose can be, but are not limited to, cellulose acetate pthalate, Eudragit L, Eudragit S, Eudragit FS, and other pthalate salts of cellulose derivatives.

These materials can be present in concentrations from 4-30% (W/W) or more. Preferably the materials are present in an amount just enough to provide the desired in vivo lag time and $T_{max}$.

As hereinabove indicated, the units comprising the amoxicillin composition of the present invention can be in the form of discrete pellets or particles contained in a capsule, or particles embedded in a tablet or suspended in a liquid suspension.

The amoxicillin products of the present invention may be administered, for example, by any of the following routes of administration: sublingual, transmucosal, transdermal, parenteral, etc., and preferably are administered orally. The product includes a therapeutically effective amount of the amoxicillin, which amount will vary with the disease or infection to be treated, and the number of times that the product is to be delivered in a day. The product is administered to a patient or subject (i.e., a human or an animal) in an amount effective for treating a bacterial infection.

In accordance with one embodiment, the amoxicillin product has an overall release profile such that when administered to a human the maximum plasma concentration of the total amoxicillin released from the product is reached in less than twelve hours, preferably in less than eleven hours.

In a further aspect, the present invention provides a method of treating various infections in a human, caused by bacterial pathogens, which treating comprises administering to the patient, or to the subject, the herein described amoxicillin product. As non-limiting examples of the indications for which the amoxicillin product may be used to treat a patient there may be mentioned: pharyngitis, tonsillitis, sinusitis, bronchitis, pneumoniae, ear infection (otitis media), uncomplicated skin and skin structure infections, and uncomplicated urinary infections.

As non-limiting examples of the infectious bacterial pathogens against which the amoxicillin products may be used, there may be mentioned Gram-Positive Aerobes such as *Staphylococcus aureus, Enterococcus faecalis, Staphylococcus epidermidis, Staphylococcus saprophyticus, Streptococcus pneumoniae, Streptococcus pyogenes*, and viridans group *Streptococcus*; Gram-Negative Aerobes such as *Enterobacter* species, *Escherichia coli, Haemophilus influenzae, Klebsiella* species, *Moraxella catarrhalis, Eikenella corrodens, Neisseria gonorrhoeae*, and *Proteus mirabilis*; Anaerobic Bacteria such as *Bacteroides* species, including *Bacteroides fragilis, Fusobacterium* species, and *Peptostreptococcus* species.

In one embodiment the amoxicillin product is formulated to specifically target tonsillopharyngitis secondary to *Streptococcus pyogenes*.

It will be appreciated by those of ordinary skill in the art that the methods and formulations described for the amoxicillin products are also applicable to amoxicillin in combination with clavulanate, or in combination with other beta-lactamase inhibitors, particularly for treating infections where beta-lactamase producing pathogens are implicated as the primary infection or as a co-infection.

In treating a bacterial infection, the amoxicillin product is formulated to provide a concentration of amoxicillin in the plasma that is above the MIC of the bacterial pathogen for a period of time each day that is effective for treating the bacterial infection. The amoxicillin product is administered for a number of days that provides a concentration of MIC in the plasma for a total time over MIC (daily time over MIC multiplied by the number of days of treatment) that is effective for treating the bacterial infection.

The invention will be further described with respect to the following Examples; however, the scope of the invention is not limited by such Examples. Unless otherwise specified parts and percentages are by weight.

EXAMPLE 1

A single dose pharmacokinetic study in human subjects is utilized to characterize the performance of the amoxicillin modified release product.

(a) Fed State Regimen

High Fat Regimen:

While administering the experimental study medication, under high fat meal conditions, all subjects will be required to fast for at least 10 hours until 30 minutes prior to their scheduled dosing times, when they will be given a high-fat (approximately 50% of total caloric content of the meal) and high-calorie (approximately 800 to 1000 calories) breakfast which will be entirely consumed within 30 minutes. The breakfast will consist of 2 slices of buttered toast, 2 fried eggs, 2 strips of bacon, 1 serving of hash brown potatoes, and 240 mL of whole milk. The study medication will be administered with 240 mL of water. Water will be allowed ad lib during the study, except for 1 hour pre-dose through 1 hour post-dose. All subjects will continue to fast through at least 4 hours following drug administration.

Low Fat Regimen:

While administering the experimental study medication under standardized meal conditions, all subjects will be required to fast for at least 10 hours until 30 minutes prior to their scheduled dosing times, when they will be given a standardized breakfast (approximately 25-30% of total caloric content of meal from fat and a total of approximately 470 calories), which will be entirely consumed within 30 minutes. The breakfast will consist of 2 slices of toast with 1 tablespoon of butter, 1 ounce of cornflake cereal in 120 mL of whole milk, 150 mL of orange juice. The study medication will be administered with 240 mL of water. Water will be allowed ad lib during the study, except for 1 hour pre-dose through 1 hour post-dose. All subjects will continue to fast through at least 4 hours following drug administration.

(b) Fasted Regimen:

While administering the experimental study medication under fasting conditions, all subjects will be required to fast for at least 10 hours prior to dosing. Water will be allowed during the study, except for 1 hour pre-dose through 1 hour post-dose. All subjects will continue to fast through at least 4 hours following drug administration.

(c) Drug Administration Protocol

While under fed conditions, each subject will receive an oral amoxicillin product administered with 240 mL of tap water in the morning at Hour 0, 30 minutes after administration of a high-fat/high-calorie breakfast or a low fat/standardized breakfast as per study randomization.

Typical clinical study site meals will be provided 4 and 9-hours after dosing, and at appropriate times thereafter. The same menu and meal schedule is to be administered uniformly for all subjects.

Beverages containing alcohol, caffeine, xanthine and/or grapefruit will be restricted during the confinement period of the study.

A compliance check of the hand and mouth will be performed to ensure ingestion of each dose.

Subjects will remain ambulatory or seated upright for the first 4 hours after drug administration. However, should adverse events occur at any time, subjects may be placed in an appropriate position or will be permitted to lie down on their right side. Subjects will not engage in strenuous activity at any time during the confinement period.

(d) Blood Sampling Protocol

Blood samples (3 mL) will be drawn in lavender top/EDTA vacutainer tubes at the following times: Pre-dose (Hour 0) and 0.5, 1, 1.5, 2, 2.5, 3, 3.5, 4, 4.5, 5, 5.5, 6, 6.5, 7, 8, 10, 12, 14, 16, and 24 hours post-dose. Intravenous catheters may be used as an alternative for straight needle sticks.

There will be 21 blood samples collected during each period for a total of 63 blood samples per subject. As a result, the subjects will have 189 mL of blood collected during the study for drug analysis and 60 mL of blood (15 mL at screening and 15 mL at end of each period or upon early termination) for clinical laboratory evaluation. An additional 20 mL (5 mL at screening and 5 mL at each check-in) will be collected from females for serum pregnancy testing.

Blood samples will be stored on ice prior to processing and storing (fluorescent lighting acceptable). Plasma samples will be separated by centrifugation (approximately 2500 rpm×15 minutes at 4° C.) as soon as possible (within 30 minutes). The plasma from each sample should be aliquotted in approximately equal volume into duplicate tubes (minimum of 0.5 mL per tube). Within approximately 90 minutes of collection, samples will be stored in clearly labeled containers (polypropylene) in a freezer set at or below −80° C., until shipped for assay. The sample storage containers will be labeled with clinical study site standard bar-code labels.

At the end of the period, samples will be shipped on dry ice via overnight courier to the bioanalytical laboratory for analysis.

(e) Bio-Analytical Method for Plasma Analysis

Plasma samples are analyzed using a bioanalytical method suitable for amoxicillin that is validated over the range of 0.05 μg/mL-25 μg/mL in accordance with the FDA Guidance for Industry—Bioanalytical Method Validation, May, 2001.

(f) Method for Calculating Partial AUCs

For partial AUC calculations the standard linear trapezoidal summation over each time interval is used. The partial AUCs are calculated from the mean pharmacokinetic profile, e.g. a single mean PK profile is calculated as the average amoxicillin plasma concentration of all subjects at each timepoint. For time 0 to 2 hours the partial AUC is $AUC_{(0-2)}$ and for time 2 to 5 hours the partial AUC is $AUC_{(2-5)}$ and for time 5-12 hours the partial AUC is $AUC_{(5-12)}$ where each partial AUC is calculated according to standard pharmaceutical industry pharmacokinetic calculation methodologies as given by:

$AUC_{(0-2)}$ Area under the drug concentration-time curve calculated using linear trapezoidal summation from time zero to time 2 hours.

$AUC_{(2-5)}$ Area under the drug concentration-time curve calculated using linear trapezoidal summation from time 2 hours to time 5 hours.

$AUC_{(5-12)}$ Area under the drug concentration-time curve calculated using linear trapezoidal summation from time 5 hours to time 12 hours.

The ratios are then calculated by dividing each of the $AUC_{(2-5)}$ value and the $AUC_{(5-12)}$ value by the $AUC_{(0-20)}$ value.

EXAMPLE 2

Formulation

An amoxicillin tablet (Applicants' MP) is made that incorporates an immediate release component (Pulse 1); a first delayed release component (Pulse 2) and a second delayed release component (Pulse 3). The tablet rapidly disintegrates upon ingestion.

1. Product Description

The Applicants' MP Tablet, 775 mg, is a three-pulse dosage form. The tablet is manufactured by combining the immediate-release granulation (Pulse 1, 45%) with two functionally coated delayed-release pellets (Pulse 2, 30% and Pulse 3, 25%). A non-functional, protective film is then applied to the tablet.

The qualitative composition, the pharmaceutical grade and the function of the individual components comprising each dosage form are listed in Table 1-1.

TABLE 1-1

Qualitative Composition of Applicants' MP Tablet, 775 mg

| Component & Grade | Manufacturer | Function |
|---|---|---|
| Amoxicillin, USP | Fersinsa | API |
| Microcrystalline Cellulose, NF (Avicel PH101) | FMC | Diluent |
| Silicified Microcrystalline Cellulose (Prosolv SMCC 90) | JRS Pharma | Diluent |
| Polyoxyl 35 Castor Oil, NF (Cremophor EL) | BASF | Wetting agent |
| Povidone, USP (Kollidon 30) | BASF | Binder |
| Crospovidone, NF (Polyplasdone XL) | ISP | Disintegrant |
| Magnesium Stearate, NF | Mallinckrodt | Lubricant |
| Hypromellose Acetate Succinate, NF (AQOAT AS-HF) | Shin-Etsu | Functional film coat |

TABLE 1-1-continued

Qualitative Composition of Applicants' MP Tablet, 775 mg

| Component & Grade | Manufacturer | Function |
| --- | --- | --- |
| Methacrylic Acid Copolymer Dispersion, NF (Eudragit L30D-55) | Rohm | Functional film coat |
| Triethyl Citrate, NF | Morflex | Plasticizer |
| Talc, USP (Imperial 1885L) | Luzenac America | Antitacking agent |
| Sodium Lauryl Sulfate, NF | Spectrum | Surfactant |
| Opadry ® Clear YS-1-19025-A | Colorcon | Non-functional film coat |
| Opadry ® Blue 03B10826 | Colorcon | Non-functional film coat |

2. Quantitative Composition of Applicants' MP Tablet, 775 mg

The quantitative composition for Applicants' MP Tablet, 775 mg, amoxicillin granules, amoxicillin core pellets, and pulsatile pellets are located in Tables 2-1 through 2-5.

2.1 Applicants' MP Tablet, 775 mg

A batch of 144.9 kg of Applicants' MP Tablet, 775 mg, containing 891.2 mg of amoxicillin trihydrate, equivalent to 775 mg amoxicillin is manufactured. The total tablet weight is approximately 1.5 grams. The quantitative composition for Applicants' MP Tablet, 775 mg is listed below in Table 2-1.

TABLE 2-1

Quantitative Composition of Applicants' MP Tablet, 775 mg

| Component | w/w % |
| --- | --- |
| Amoxicillin, USP | 59.5 |
| Silicified Microcrystalline Cellulose (Prosolv SMCC 90) | 20.8 |
| Crospovidone, NF (Polyplasdone XL) | 3.9 |
| Methacrylic Acid Copolymer Dispersion, NF (Eudragit L30D-55) | 2.9* |
| Opadry ® Blue 03B10826 | 2.4 |
| Talc, USP (Imperial 1885L) | 2.0 |
| HypromelloseAcetate Succinate, NF (AQOAT AS-HF) | 1.9 |
| Microcrystalline Cellulose, NF (Avicel PH101) | 1.8 |
| Povidone, USP (PVP K30) | 1.5 |
| Opadry ® Clear YS-1-19025-A | 1.0 |
| Magnesium Stearate, NF | 1.0 |
| Triethyl Citrate, NF | 0.9 |
| Polyoxyl 35 Castor Oil, NF (Cremophor EL) | 0.3 |
| Sodium Lauryl Sulfate, NF | 0.1 |
| Opacode ® Black S-1-17734 | 0.0 |
| Total | 100.0 |

*Weight percent of solids content 2.2 Amoxicillin Trihydrate (97%) Granules

A batch of 20 kg of Amoxicillin Trihydrate (97%) Granules is manufactured. The Amoxicillin granules serve as Pulse 1 of the final formulation. The granules are compressed with Pulse 2 and 3 pellets and other inactive components to form the tablet core.

A standard wet granulation process known to one skilled in the art is used for preparation of the Amoxicillin Granules. The wet granules are discharged and fed into a Dome Extrusion Granulator. The wet extruded granules are then dried for a fixed period of time or until the LOD (loss on drying) of the granules is suitable for the formulation, typically less than 15%. The dried granules are then sized in a Rotating Impeller Screening Mill. The milled material is collected into drums. The quantitative composition for Amoxicillin Trihydrate (97%) Granules is listed below in Table 2-2.

TABLE 2-2

Quantitative Composition of Amoxicillin Trihydrate (97%) Granules (Used for Pulse 1 in compression blend)

| Component | w/w % |
| --- | --- |
| Amoxicillin, USP | 97.0 |
| Povidone, USP (Kollidon 30) | 3.0 |
| Total | 100.0 |

2.3 Amoxicillin Trihydrate (92%) Core Pellets

A batch of 20 kg Amoxicillin Trihydrate (92%) Core Pellets is manufactured. The Amoxicillin core pellets are coated with functional film coating to produce Pulse 2 and 3 pellets.

The core pellets are prepared using the unit operations of wet granulating, extruding, spheronizing, fluid bed drying and sizing. The quantitative composition for Amoxicillin Trihydrate (92%) Core Pellets is listed below in Table 2-3.

TABLE 2-3

Quantitative Composition of Amoxicillin Trihydrate (92%) Core Pellets (Used for Amoxicillin Pulse 2 and 3 Pellets)

| Component | w/w % |
| --- | --- |
| Amoxicillin, USP | 92.0 |
| Microcrystalline Cellulose, NF (Avicel PH 101) | 5.0 |
| Povidone, USP (Kollidon 30) | 2.0 |
| Polyoxyl 35 Castor Oil, NF (Cremophor EL) | 1.0 |
| Total | 100.0 |

2.4 Amoxicillin Trihydrate (76.7%) Pulse 2 Pellets

A 16.8 kg batch of Amoxicillin Trihydrate (76.7%) Pulse 2 Pellets is manufactured by applying a 20% total solids weight gain of Eudragit L30D-55 to 14.0 kg of the Amoxicillin Trihydrate (92%) Core Pellets.

The Pulse 2 Pellets are prepared by coating the previously prepared Core Pellets with a functional film coat of methacrylic acid copolymer dispersion, 20% w/w. Prior to the coating process, a dispersion of the methacrylic acid copolymer is made according to the manufacturer's instructions. The dispersion is applied to the Amoxicillin Core pellets using a Fluid Bed Bottom Spray Coater, equipped with appropriate spray nozzles and a fixed column gap distance.

The pellets are then appropriately sized. The Amoxicillin Pulse 2 Pellets may be held in ambient warehouse conditions until further processing. The quantitative composition for Amoxicillin Trihydrate (76.7%) Pulse 2 Pellets is listed below in Table 2-4.

TABLE 2-4

Quantitative Composition of Amoxicillin Trihydrate (76.7%) Pulse 2 Pellets

| Component | w/w % |
|---|---|
| Amoxicillin, USP | 76.7 |
| Microcrystalline Cellulose, NF (Avicel PH 101) | 4.2 |
| Polyoxyl 35 Castor Oil, NF (Cremophor EL) | 0.8 |
| Povidone, USP (Kollidon 30) | 1.7 |
| Methacrylic Acid Copolymer Dispersion, NF (Eudragit L30D-55) | 10.4* |
| Talc, USP | 5.2 |
| Triethyl Citrate, NF | 1.0 |
| Total | 100 |

*Weight percent of solids content 2.5 Amoxicillin Trihydrate (76.0%) Pulse 3 Pellets A 12.5 kg batch of Amoxicillin Trihydrate (73.6%) Pulse 3 Pellets is manufactured by applying a 5% total solids wt gain sub-coat of Eudragit L30D-55 and an over-coat of 20% total solids weight gain of AQOAT AS-HF to 10.0 kg of the Amoxicillin Trihydrate (92%) Core Pellet.

Prior to the subcoating process, a dispersion of the methacrylic acid copolymer is made according to the manufacturer's instructions. The second coating material is prepared according to the manufacturer's instructions. The subcoat layer is then applied to the Amoxicillin Core Pellets using the same Fluid Bed Bottom Spray Coater as used for preparation of the Pulse 2 Pellets.

The second coating dispersion is then immediately applied to the sub-coated pellets still in the Fluid Bed Bottom Spray Coater. The atomization air used for the second coating process is set at the same pressure as used for the sub coating process. The coating process is complete when all of the dispersion has been applied. Following a drying period the final coated pellets are cooled. The quantitative composition for Amoxicillin Trihydrate (73.6%) Pulse 3 Pellets is listed below in Table 2-5.

TABLE 2-5

Quantitative Composition of Amoxicillin Trihydrate (73.6%) Pulse 3 Pellets

| Component | w/w % |
|---|---|
| Amoxicillin, USP | 73.6 |
| Microcrystalline Cellulose, NF (Avicel PH 101) | 4.0 |
| Polyoxyl 35 Castor Oil, NF (Cremophor EL) | 0.8 |
| Povidone, USP (Kollidon 30) | 1.6 |
| Methacrylic Acid Copolymer Dispersion, NF (Eudragit L30D-55) | 2.5* |
| Hypromellose Acetate Succinate, NF (AQOAT AS-HF) | 9.6 |
| Talc, USP | 4.1 |
| Triethyl Citrate, NF | 3.5 |
| Sodium Lauryl Sulfate, NF | 0.3 |
| Total | 100 |

*Weight percent of solids content

For example, the above product may be used to treat *streptococcus pyogenes* in adults by administering such product to a human once-a-day for 10 days.

EXAMPLE 3

The core pellets of Part 2.3 of Example 2 are coated with a non-functional immediate release film coating to produce Pulse 1 pellets. The Pulse 1 pellets as well as Pulse 2 and Pulse 3 pellets of Example 2 are used as a sprinkle product by placing the Pulse 1, Pulse 2 and Pulse 3 pellets in a sachet, capsule or other form that can be used for simultaneous delivery of the three pulses in a particulate form. In one embodiment, Pulse 1, Pulse 2 and Pulse 3 are combined to provide 45%, 30% and 25% of Pulse 1, Pulse 2, and Pulse 3, respectively.

Such combination of Pulses 1, 2 and 3 may be formulated into a sprinkle product; e.g., a twice-a-day product that contains 475 mg or 775 mg of amoxicillin. In another embodiment, Pulse 1, 2 and 3 may be combined into a once-a-day sprinkle product that contains 775 mg or 1250 mg or 1550 mg of amoxicillin. The sprinkle product may be sprinkled over applesauce, yogurt, or other soft food for administration. The product should not be chewed or crushed.

EXAMPLE 4

The amoxicillin product of Example 2 was tested using the procedure of Example 1 and the low fat Fed State Regimen of Example 1. The following partial AUC ratios were determined for such amoxicillin product in this study.

| Study | AUC (2-5)/AUC (0-2) | AUC (5-12)/AUC (0-2) |
|---|---|---|
| 1 | 2.9:1 | 1.3:1 |

In addition, the product of Example 2 was tested using the procedure of Example 1 and in the low fat Fed State Regimen of Example 1, but in a multidose fashion. The product was administered once daily for seven days and blood draws were taken and analyzed on the first and seventh day. There was no accumulation evident at the time zero point on day seven, therefore this multidose data can be viewed as two single dose studies. Thus the partial AUC ratios were determined at both day 1 and day 7 of administration of the amoxicillin product and are provided in the table below.

| Day | AUC (2-5)/AUC (0-2) | AUC (5-12)/AUC (0-2) |
|---|---|---|
| 1 | 3.6:1 | 2.5:1 |
| 7 | 3.6:1 | 2.2:1 |

EXAMPLE 5

The amoxicillin product of Example 2 was tested using the procedure of Example 1 with the high fat Fed State Regimen.

The following partial AUC ratios were as follows:

| $AUC_{(2-5)}/AUC_{(0-2)}$ | $AUC_{(5-12)}/AUC_{(0-2)}$ |
|---|---|
| 2.7:1 | 1.7:1 |

EXAMPLE 6

The amoxicillin product of Example 2 was tested using the procedure of Example 1 in the fasted, low fat Fed State, and high fat Fed State. The $AUC_{o-inf}$ for each of the fasted, low fat fed and high fatted tests was about 31.5 µg*hour/mL.

EXAMPLE 7

The product of Example 2 was tested in accordance with the procedure of Example 1 except the dosage of amoxicillin was 1550 mg in one regimen (2×) and 2325 mg in a second regimen (3×)

| Dose | Fed State Regimen | $AUC_{(2-5)}/AUC_{(0-2)}$ | $AUC_{(5-12)}/AUC_{(0-2)}$ |
|---|---|---|---|
| 2×-1550 mg | High Fat | 2.4:1 | 1.6:1 |
| 2×-1550 mg | Low Fat | 5.0:1 | 2.5:1 |
| 3×-2325 mg | High Fat | 2.8:1 | 1.6:1 |

Numerous modifications and variations of the present invention are possible in light of the above teachings; therefore, except as set forth in the claims the invention is not limited to described embodiments.

We claim:

1. A once-a-day amoxicillin product comprising: an immediate release component that includes amoxicillin and at least one modified release component, wherein the at least one modified release component comprises a first delayed release component that comprises amoxicillin coated with methacrylic acid copolymer dispersion and that initiates release of amoxicillin after the immediate release component, and a second delayed release component that comprises amoxicillin coated with a methacrylic acid copolymer dispersion and hypromellose acetate succinate and that initiates release of amoxicillin after the first delayed release component; said product when administered as a single dose in the fed state having: (a) a ratio of $AUC_{(2-5)}$ to $AUC_{(0-2)}$ of at least 2.0:1 and (b) a ratio of $AUC_{(5-12)}$ to $AUC_{(0-2)}$ of at least 1.1:1, and wherein $AUC_{(2-5)}$ to $AUC_{(0-2)}$ ratio is no greater than 10:1 and the $AUC_{(5-12)}$ to $AUC_{(0-2)}$ ratio is no greater than 10:1 and wherein the product is a once-a-day product.

2. The amoxicillin product of claim 1, wherein said product when administered as a single dose either in the fed state or the fasted state has an $AUC_{0-inf}$ of at least 75% of the $AUC_{0-inf}$ of an immediate release amoxicillin product, wherein the $AUC_{0-inf}$ of said immediate release amoxicillin product is determined in either the fed state or the fasted state.

3. The product of claim 1, wherein the product contains about from about 200 mg to about 2500 mg of amoxicillin.

4. The product of claim 1, wherein the product contains about 775 mg of amoxicillin.

5. The amoxicillin product of claim 1, wherein said product when administered as a single dose in the fed state has: (1) ratio of AUC(2-5) to AUC(0-2) of at least 2.2:1 and (b) a ratio of AUC(5-12) to AUC(0-2) of at least 1.2:1.

6. The product of claim 5 wherein the $AUC_{(2-5)}$ to $AUC_{(0-2)}$ ratio is no greater than 10:1 and the $AUC_{(5-12)}$ to $AUC_{(0-2)}$ ratio is no greater than 10:1.

7. The product of claim 5 wherein the product contains about from about 200 mg to about 2500 mg of amoxicillin.

8. The product of claim 5 wherein the product contains about 775 mg of amoxicillin.

9. The amoxicillin product of claim 1, wherein said product when administered as a single dose in the fed state having: (a) a ratio of $AUC_{(2-5)}$ to $AUC_{(0-2)}$ of at least 1.2:1 and (b) a ratio of $AUC_{(5-12)}$ to $AUC_{(0-2)}$ of at least 2.4:1.

10. The amoxicillin product of claim 2, wherein said product when administered as a single dose in the fed state has: (a) a ratio of $AUC_{(2-5)}$ to $AUC_{(0-2)}$ ratio of at least 2.4:1 and (b) a ratio of $AUC_{(5-12)}$ to $AUC_{(0-2)}$ of at least 1.3:1.

11. The amoxicillin product of claim 1, said amoxicillin product when administered as a single dose having: (a) a ratio of $AUC_{(2-5)}$ to $AUC_{(0-2)}$ ratio of at least 2.4:1 and (b) a ratio of $AUC_{(5-12)}$ to $AUC_{(0-2)}$ of at least 1.3:1.

12. The product of claim 11 wherein the product contains about from about 200 mg to about 2500 mg of amoxicillin.

13. The product of claim 11 wherein the product contains about 775 mg of amoxicillin.

14. A process for treating a bacterial infection in a patient or a subject comprising: administering to a patient or a subject the product of claim 1.

15. A process for treating a bacterial infection in a patient or a subject comprising: administering to a patient or a subject the product of claim 2.

16. A process for treating a bacterial infection in a patient or a subject comprising: administering to a patient or a subject the product of claim 3.

17. A process for treating a bacterial infection in a patient or a subject comprising: administering to a patient or a subject the product of claim 4.

18. A process for treating a bacterial infection in a patient or a subject comprising: administering to a patient or a subject the product of claim 5.

19. A process for treating a bacterial infection in a patient or a subject comprising: administering to a patient or a subject the product of claim 6.

20. A process for treating a bacterial infection in a patient or a subject comprising: administering to a patient or a subject the product of claim 7.

21. A process for treating a bacterial infection in a patient or a subject comprising: administering to a patient or a subject the product of claim 8.

22. A process for treating a bacterial infection in a patient or a subject comprising: administering to a patient or a subject the product of claim 9.

23. A process for treating a bacterial infection in a patient or a subject comprising: administering to a patient or a subject the product of claim 10.

24. A process for treating a bacterial infection in a patient or a subject comprising: administering to a patient or a subject the product of claim 11.

25. A process for treating a bacterial infection in a patient or a subject comprising: administering to a patient or a subject the product of claim 12.

26. A process for treating a bacterial infection in a patient or a subject comprising: administering to a patient or a subject the product of claim 13.

27. The product of claim 1, wherein the product having an equivalent extent of absorption when administered in both the fasted and fed states.

28. A process for treating a bacterial infection in a patient or a subject comprising: administering to a patient or a subject the product of claim 27.

29. The product of claim 1, further comprising clavulanate or other beta-lactamase inhibitor.

30. The product of claim 2, further comprising clavulanate or other beta-lactamase inhibitor.

31. The product of claim 5, further comprising clavulanate or other beta-lactamase inhibitor.

32. The product of claim 9, further comprising clavulanate or other beta-lactamase inhibitor.

33. The product of claim 10, further comprising clavulanate or other beta-lactamase inhibitor.

34. The product of claim 11, further comprising clavulanate or other beta-lactamase inhibitor.

35. The product of claim 27, further comprising clavulanate or other beta-lactamase inhibitor.

36. A process for treating a bacterial infection in a patient or a subject comprising: administering to a patient or a subject the product of claim 29.

37. A process for treating a bacterial infection in a patient or a subject comprising: administering to a patient or a subject the product of claim 30.

38. A process for treating a bacterial infection in a patient or a subject comprising: administering to a patient or a subject the product of claim 31.

39. A process for treating a bacterial infection in a patient or a subject comprising: administering to a patient or a subject the product of claim 32.

40. A process for treating a bacterial infection in a patient or a subject comprising: administering to a patient or a subject the product of claim 33.

41. A process for treating a bacterial infection in a patient or a subject comprising: administering to a patient or a subject the product of claim 34.

42. A process for treating a bacterial infection in a patient or a subject comprising: administering to a patient or a subject the product of claim 35.

43. The product of claim 1, wherein the immediate release component about 45% of the total amoxicillin dose in the product, the first delayed release component comprises about 30% of the total amoxicillin dose in the product, and the second delayed release component comprises about 25% of the total amoxicillin dose in the product.

44. The product of claim 1, wherein the immediate release component further comprises povidone.

45. The product of claim 1, wherein the first delayed release component further comprises microcrystalline cellulose, povidone, castor oil, talc, and triethyl citrate.

46. The product of claim 1, wherein the second delayed release component further comprises microcrystalline cellulose, povidone, castor oil, talc, triethyl citrate, and sodium lauryl sulfate.

47. The product of claim 43, wherein the immediate release component further comprises povidone.

48. The product of claim 43, wherein the first delayed release component further comprises microcrystalline cellulose, povidone, castor oil, talc, and triethyl citrate.

49. The product of claim 48, wherein the second delayed release component further comprises microcrystalline cellulose, povidone, castor oil, talc, triethyl citrate, and sodium lauryl sulfate.

50. The product of claim 43 wherein the product contains about from about 200 mg to about 2500 mg of amoxicillin.

51. The product of claim 43 wherein the product contains 775 mg of amoxicillin.

52. A process for treating a bacterial infection in a patient or a subject comprising: administering to a patient or a subject the product of claim 43.

53. A process for treating a bacterial infection in a patient or a subject comprising: administering to a patient or a subject the product of claim 44.

54. A process for treating a bacterial infection in a patient or a subject comprising: administering to a patient or a subject the product of claim 45.

55. A process for treating a bacterial infection in a patient or a subject comprising: administering to a patient or a subject the product of claim 46.

56. A process for treating a bacterial infection in a patient or a subject comprising: administering to a patient or a subject the product of claim 47.

57. A process for treating a bacterial infection in a patient or a subject comprising: administering to a patient or a subject the product of claim 48.

58. A process for treating a bacterial infection in a patient or a subject comprising: administering to a patient or a subject the product of claim 49.

59. A process for treating a bacterial infection in a patient or a subject comprising: administering to a patient or a subject the product of claim 50.

60. A process for treating a bacterial infection in a patient or a subject comprising: administering to a patient or a subject the product of claim 51.

* * * * *